(12) United States Patent
Cui et al.

(10) Patent No.: US 12,346,799 B2
(45) Date of Patent: Jul. 1, 2025

(54) OPTICAL ARTIFICIAL NEURAL NETWORK INTELLIGENT CHIP, PREPARATION METHOD THEREOF AND INTELLIGENT PROCESSING APPARATUS

(71) Applicant: Tsinghua University, Beijing (CN)

(72) Inventors: Kaiyu Cui, Beijing (CN); Jiawei Yang, Beijing (CN); Jian Xiong, Beijing (CN); Yidong Huang, Beijing (CN); Fang Liu, Beijing (CN); Xue Feng, Beijing (CN); Wei Zhang, Beijing (CN)

(73) Assignee: Tsinghua University, Beijing (CN)

( * ) Notice: Subject to any disclaimer, the term of this patent is extended or adjusted under 35 U.S.C. 154(b) by 880 days.

(21) Appl. No.: 17/377,217

(22) Filed: Jul. 15, 2021

(65) Prior Publication Data
US 2022/0253686 A1    Aug. 11, 2022

(30) Foreign Application Priority Data

Feb. 8, 2021   (CN) .......................... 202110172841.0

(51) Int. Cl.
*G06N 3/00*      (2023.01)
*G06N 3/048*    (2023.01)
(Continued)

(52) U.S. Cl.
CPC .......... *G06N 3/0675* (2013.01); *G06N 3/048* (2023.01); *G06N 3/063* (2013.01); *G06N 3/08* (2013.01)

(58) Field of Classification Search
CPC .......... G06N 3/063; G06N 3/08; G06N 3/044; G06N 3/045; G06N 3/084; G06N 3/10;
(Continued)

(56) References Cited

U.S. PATENT DOCUMENTS 5,080,464 A * 1/1992 Toyoda ................ G06N 3/0675
                                                      359/107
5,255,362 A * 10/1993 Brandstetter ........ G06N 3/0675
                                                      382/158
(Continued)

FOREIGN PATENT DOCUMENTS

CN        110133782 A      8/2019
CN        110806640 A *    2/2020    ............. G02B 27/00
(Continued)

OTHER PUBLICATIONS

A Review of Optical Neural Networks (Year: 2020).*
(Continued)

*Primary Examiner* — Mohamed Abou El Seoud
(74) *Attorney, Agent, or Firm* — Dickinson Wright PLLC

(57) ABSTRACT

An optical artificial neural network intelligent chip, a preparation method thereof and an intelligent processing apparatus. The optical filter layer serves as the input layer of the artificial neural network. The image sensor serves as the linear layer of the artificial neural network. The filtering effect of the optical filter layer on the incident light entering the optical filter layer serves as the connection weight from the input layer to the linear layer, such that the related functions of the input layer and the linear layer in the artificial neural network are achieved by the optical filter layer and the image sensor in the intelligent chip in a hardware manner, and no complicated signal processing and algorithm processing corresponding to the input layer and the linear layer need to be performed in the subsequent artificial neural network intelligent processing using the intelligent chip.

25 Claims, 11 Drawing Sheets

(51) Int. Cl.
    *G06N 3/063*     (2023.01)
    *G06N 3/067*     (2006.01)
    *G06N 3/08*     (2023.01)

(58) Field of Classification Search
    CPC .... G06N 3/0675; G06N 3/048; G06N 3/0895; G06N 3/09; G06N 3/091; G06N 3/092; G06N 3/094; G06N 3/096; G06N 3/098; G06N 3/0985; A61B 5/14532; G06F 18/00
    See application file for complete search history.

(56) References Cited

U.S. PATENT DOCUMENTS

| | | | |
|---|---|---|---|
| 10,217,023 B1* | 2/2019 | Rubin | G06N 3/04 |
| 11,392,830 B2* | 7/2022 | Ozcan | G06N 3/082 |
| 2019/0019100 A1* | 1/2019 | Roques-Carmes | G06N 3/0675 |

FOREIGN PATENT DOCUMENTS

| | | |
|---|---|---|
| CN | 110866601 A | 3/2020 |
| CN | 111458777 A | 7/2020 |
| WO | WO2019200289 A1 | 10/2019 |
| WO | WO-2022041069 A1 * | 3/2022 |

OTHER PUBLICATIONS

China National Intellectual Property Administration, Search Report and Written Opinion for International Application No. PCT/CN2021/115965, Form 210, Date of Mailing Dec. 2, 2021, 2 pages.

* cited by examiner

OPTICAL ARTIFICIAL NEURAL NETWORK INTELLIGENT CHIP, PREPARATION METHOD THEREOF AND INTELLIGENT PROCESSING APPARATUS

CROSS-REFERENCE TO RELATED APPLICATIONS

The present application claims priority to Chinese Patent Application No. 202110172841.0 filed on Feb. 8, 2021, entitled "Optical Artificial Neural Network Intelligent Chip, Preparation Method thereof and Intelligent Processing Apparatus", which is hereby incorporated by reference in its entirety.

FIELD OF TECHNOLOGY

The present application relates to the technical field of artificial intelligence, in particular to an optical artificial neural network intelligent chip, a preparation method thereof and an intelligent processing apparatus.

BACKGROUND

Traditional intelligent recognition technologies are to recognize people or objects usually by imaging people or objects firstly, and then performing steps of image preprocessing, feature extraction, feature matching, etc. However, it is difficult to ensure the accuracy of recognition using only the two-dimensional image information of people or objects, for example, it is difficult to distinguish between real faces and photos of faces. Also, during the imaging process, optical information needs to be converted into digital electronic signals, and then transmitted to a computer for subsequent algorithm processing. Therefore, the transmission and processing of a large amount of data causes greater power consumption and delay.

SUMMARY

Embodiments of the present application provide an optical artificial neural network intelligent chip, a preparation method thereof and an intelligent processing apparatus.

Specifically, the embodiments of the present application provide the following technical solutions.

In a first aspect, an embodiment of the present application provides an optical artificial neural network intelligent chip, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation stricture, to obtain information carried in the incident light corresponding to different location points on the surface of the photosensitive area; the information carried in the incident light includes light intensity distribution information, spectral information, angle information of the incident light and phase information of the incident light;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer; and the processor is configured to perform fully connected processing and nonlinear activation processing on the electrical signals corresponding to the different location points to obtain output signals of the artificial neural network.

In an embodiment, the optical artificial neural network intelligent chip is used for intelligent processing tasks of a target object; the intelligent processing tasks include at least one or more of an intelligent perception task, an intelligent recognition task and an intelligent decision task;

reflected light, transmitted light and/or radiation light of the target object enters a trained optical artificial neural network intelligent chip to obtain intelligent processing results of the target object; the intelligent processing results include at least one or more of an intelligent perception result, an intelligent recognition result and/or an intelligent decision result.

The trained optical artificial neural network intelligent chip refers to an optical artificial neural network intelligent chip including a trained optical modulation structure, an image sensor and a processor; the trained optical modulation structure, the image sensor and the processor refer to an optical modulation structure, an image sensor and an processor satisfying a training convergence condition obtained by training the optical artificial neural network intelligent chip containing different optical modulation structures, image sensors, and processors with different fully connected parameters and nonlinear activation parameters using input training samples and output training samples corresponding to the intelligent processing task.

In an embodiment, when the optical artificial neural network intelligent chip containing different optical modulation structures, image sensors, and processors with different fully connected parameters and nonlinear activation parameters is trained, the different optical modulation structures are designed and implemented in a computer optical simulation design manner.

In an embodiment, the optical modulation structure in the optical filter layer includes a regular structure and/or an irregular structure; and/or, the optical modulation structure in the optical filter layer includes a discrete structure and/or a continuous structure.

In an embodiment, the optical filter layer has a single-layer structure or a multi-layer structure.

In an embodiment, the optical modulation structure in the optical filter layer includes a unit array composed of a plurality of micro-nano units, and each micro-nano unit corresponds to one or more pixels on the image sensor; each micro-nano unit has the same or different structure.

In an embodiment, the micro-nano unit includes a regular structure and/or an irregular structure; and/or the micro-nano unit includes a discrete structure and/or a continuous structure.

In an embodiment, the micro-nano unit includes a plurality of groups of micro-nano structure arrays, and each group of the micro-nano structure arrays has the same or different structure._

In an embodiment, each group of micro-nano structure array has broadband filtering or narrowband filtering functions.

In an embodiment, each group of micro-nano structure arrays is a periodic structure array or an aperiodic structure array.

In an embodiment, the plurality of groups of micro-nano structure arrays contained in the micro-nano unit has one or more groups of empty structures.

In an embodiment, the micro-nano unit has polarization-independent characteristics.

In an embodiment, the micro-nano unit has four-fold rotation symmetry.

In an embodiment, the optical filter layer is composed of one or more filter layers;

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

In an embodiment, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nanopillar two-dimensional materials, and nanowire two-dimensional materials.

In an embodiment, the optical filter layer has a thickness of $0.1\lambda$-$10\lambda$, where $\lambda$ represents the center wavelength of the incident light.

In an embodiment, the image sensor is any one or more of the following:

CMOS image sensor (CIS), charge coupled device (CCD), single photon avalanche diode (SPAD) array and focal plane photodetector array.

In an embodiment, the types of the artificial neural network include feedforward neural network.

In an embodiment, a light-permeable medium layer is provided between the optical filter layer and the image sensor.

In an embodiment, the image sensor is front-side illuminated type, and includes a metal wire layer and a light detection layer arranged from top to bottom, and the optical filter layer is integrated on a side of the metal wire layer away from the light detection layer.

Alternatively, the image sensor is back-side illuminated type, and includes a light detection layer and a metal wire layer arranged from top to bottom, and the optical filter layer is integrated on a side of the light detection layer away from the metal wire layer.

In a second aspect, an embodiment of the present application provides an intelligent processing apparatus, including the optical artificial neural network intelligent chip as described in the first aspect.

In an embodiment, the intelligent processing apparatus includes one or more of smart phones, smart computers, intelligent identification devices, intelligent perception devices, and intelligent decision devices.

In a third aspect, an embodiment of the present application provides a method for preparing an optical artificial neural network intelligent chip, including:

preparing an optical filter layer containing an optical modulation structure on a surface of a photosensitive area of an image sensor;

generating a processor with the functions of fully connected processing and nonlinear activation processing of signals; and connecting the image sensor and the processor;

wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light;

the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain output signals of the artificial neural network; and the electrical signals are image signals modulated by the optical filter layer.

In an embodiment, the preparing an optical filter layer containing an optical modulation structure on a surface of a photosensitive area of an image sensor includes:

growing one or more layers of preset materials on the surface of the photosensitive area of the image sensor;

etching a pattern of the optical modulation structure on the one or more layers of preset materials to obtain the optical filter layer containing the optical modulation structure; or performing imprint transfer on the one or more layers of preset materials to obtain the optical filter layer containing the optical modulation structure; or performing additional dynamic modulation on the one or more layers of preset materials to obtain the optical filter layer containing the optical modulation structure; or performing zonal printing on the one or more layers of preset materials to obtain the optical filter layer containing the optical modulation structure; or performing zonal growth on the one or more layers of preset materials to obtain the optical filter layer containing the optical modulation structure; or performing quantum dot transfer on the one or more layers of preset materials to obtain the optical filter layer containing the optical modulation structure.

In an embodiment, when the optical artificial neural network intelligent chip is used for the intelligent processing task of the target object, an optical modulation structure, an image sensor and an processor satisfying the training convergence condition are obtained by training the optical artificial neural network intelligent chip containing different optical modulation structures, image sensors, and processors with different fully connected parameters and nonlinear activation parameters using input training samples and output training samples corresponding to the intelligent processing task.

An embodiment of the present application also provides an optical artificial neural network face recognition chip for face recognition processing tasks, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and the incident light is the reflected light of the user's face;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer; and the processor is configured to perform fully connected processing and nonlinear activation processing on the electrical signals corresponding to the different location points to obtain face recognition processing results.

In an embodiment, the optical artificial neural network face recognition chip includes a trained optical modulation structure, an image sensor and a processor;

the trained optical modulation structure, an image sensor and a processor refer to an optical modulation structure, an image sensor and an processor satisfying the training convergence condition obtained by training the optical artificial neural network face recognition chip containing different optical modulation structures, image sensors, and processors with different fully connected parameters and different nonlinear activation parameters using input training samples and output training samples corresponding to a face recognition task; and the input training samples include incident light reflected by different faces under different light environments; the output training samples include corresponding face recognition results.

In an embodiment, when the optical artificial neural network face recognition chip containing different optical modulation structures, image sensors, and processors with different fully connected parameters and nonlinear activation parameters is trained, the different optical modulation structures are designed and implemented in a computer optical simulation design manner.

In an embodiment, the optical modulation structure in the optical filter layer includes a regular structure and/or an irregular structure; and/or, the optical modulation structure in the optical filter layer includes a discrete structure and/or a continuous structure.

In an embodiment, the optical filter layer has a single-layer structure or a multi-layer structure.

In an embodiment, the optical modulation structure in the optical filter layer includes a unit array composed of a plurality of micro-nano units, and each micro-nano unit corresponds to one or more pixels on the image sensor; each micro-nano unit has the same or different structure.

In an embodiment, the micro-nano unit includes a regular structure and/or an irregular structure; and/or the micro-nano unit includes a discrete structure and/or a continuous structure.

In an embodiment, the micro-nano unit includes a plurality of groups of micro-nano structure arrays, and each group of the micro-nano structure arrays has the same or different structure.

In an embodiment, each group of micro-nano structure array has broadband filtering or narrowband filtering functions.

In an embodiment, each group of micro-nano structure arrays is a periodic structure array or an aperiodic structure array.

In an embodiment, the plurality of groups of micro-nano structure arrays contained in the micro-nano unit has one or more groups of empty structures.

In an embodiment, the micro-nano unit has polarization-independent characteristics.

In an embodiment, the polarization-independent micro-nano unit has four-fold rotation symmetry.

In an embodiment, the optical filter layer is composed of one or more filter layers;

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

In an embodiment, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nanopillar two-dimensional materials, and nanowire two-dimensional materials.

In an embodiment, the optical filter layer has a thickness of $0.1\lambda$-$10\lambda$, where $\lambda$ represents the center wavelength of the incident light.

An embodiment of the present application also provides a face recognition apparatus, including the optical artificial neural network face recognition chip as described above.

An embodiment of the present application also provides a method for preparing the optical artificial neural network face recognition chip as described above, including:

preparing an optical filter layer containing an optical modulation structure on a surface of a photosensitive area of an image sensor;

generating a processor with the functions of fully connected processing and nonlinear activation processing of signals; and connecting the image sensor and the processor;

wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light;

the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain face recognition processing results; and the electrical signals are image signals modulated by the optical filter layer and the incident light is the reflected light of the user's face under different light environments.

In an embodiment, the method for preparing the optical artificial neural network face recognition chip further includes a training process of the optical artificial neural network face recognition chip and specifically includes:

training the optical artificial neural network face recognition chip containing different optical modulation structures, image sensors, and processors with different fully connected parameters and different nonlinear activation parameters using input training samples and output training samples corresponding to the face recognition task to obtain an optical modulation structure, an image sensor and an processor satisfying the training convergence condition and taking the optical modulation structure, the image sensor and the processor satisfying the training convergence condition as the trained optical modulation structure, the image sensor and the processor.

In an embodiment, when the optical artificial neural network face recognition chip containing different optical modulation structures, image sensors, and processors with different fully connected parameters and nonlinear activation parameters is trained, the different optical modulation structures are designed and implemented in a computer optical simulation design manner.

An embodiment of the present application also provides an optical artificial neural network blood glucose detection chip for blood glucose detection tasks, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; wherein the incident light includes reflected light and/or transmitted light of a part of the human body to be detected;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer; and the processor is configured to perform fully connected processing and nonlinear activation processing on the electrical signals corresponding to the different location points to obtain blood glucose detection results.

In an embodiment, the optical artificial neural network blood glucose detection chip includes a trained optical modulation structure, an image sensor and a processor;

the trained optical modulation structure, an image sensor and a processor refer to an optical modulation structure, an image sensor and an processor satisfying the training convergence condition obtained by training the optical artificial neural network blood glucose detection chip containing different optical modulation structures, image sensors, and processors with different fully connected parameters and different nonlinear activation parameters using input training samples and output training samples corresponding to the blood glucose detection tasks; and the input training samples include incident light reflected and transmitted by parts of the human body to be detected with different blood glucose values; the output training samples include corresponding blood glucose values.

In an embodiment, when the optical artificial neural network blood glucose detection chip containing different optical modulation structures, image sensors, and processors with different fully connected parameters and nonlinear activation parameters is trained, the different optical modulation structures are designed and implemented in a computer optical simulation design manner.

In an embodiment, the optical modulation structure in the optical filter layer includes a regular structure and/or an irregular structure; and/or, the optical modulation structure in the optical filter layer includes a discrete structure and/or a continuous structure.

In an embodiment, the optical filter layer has a single-layer structure or a multi-layer structure.

In an embodiment, the optical modulation structure in the optical filter layer includes a unit array composed of a plurality of micro-nano units, and each micro-nano unit corresponds to one or more pixels on the image sensor; each micro-nano unit has the same or different structure.

In an embodiment, the micro-nano unit includes a regular structure and/or an irregular structure; and/or the micro-nano unit includes a discrete structure and/or a continuous structure.

In an embodiment, the micro-nano unit includes a plurality of groups of micro-nano structure arrays, and each group of the micro-nano structure arrays has the same or different structure.

In an embodiment, each group of micro-nano structure array has the broadband filtering or narrowband filtering functions.

In an embodiment, each group of micro-nano structure arrays is a periodic structure array or an aperiodic structure array.

In an embodiment, the plurality of groups of micro-nano structure arrays contained in the micro-nano unit has one or more groups of empty structures.

In an embodiment, the micro-nano unit has polarization-independent characteristics.

In an embodiment, the polarization-independent micro-nano unit has four-fold rotation symmetry.

In an embodiment, the optical filter layer is composed of one or more filter layers;

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

In an embodiment, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nanopillar two-dimensional materials, and nanowire two-dimensional materials.

In an embodiment, the optical filter layer has a thickness of $0.1\lambda$-$10\lambda$, where $\lambda$ represents the center wavelength of the incident light.

An embodiment of the present application also provides an intelligent blood glucose detector, including the optical artificial neural network blood glucose detection chip as described above.

An embodiment of the present application also provides a method for preparing the optical artificial neural network blood glucose detection chip as described above, including:

preparing an optical filter layer containing an optical modulation structure on a surface of a photosensitive area of an image sensor;

generating a processor with the functions of fully connected processing and nonlinear activation processing of signals; and connecting the image sensor and the processor;

wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light;

the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain blood glucose detection results; and the electrical signals are image signals modulated by the optical filter layer and the incident light includes reflected light and/or transmitted light of a part of the human body to be detected.

In an embodiment, the method for preparing the optical artificial neural network blood glucose detection chip further includes a training process of the optical artificial neural network blood glucose detection chip and specifically includes:

training the optical artificial neural network blood glucose detection chip containing different optical modulation structures, image sensors, and processors with different fully connected parameters and different nonlinear activation parameters using input training samples and output training samples corresponding to the blood glucose detection task to obtain an optical modulation structure, an image sensor and an processor satisfying the training convergence condition and taking the optical modulation structure, the image sensor and the processor satisfying the training convergence condition as the trained optical modulation structure, the image sensor and the processor.

In an embodiment, when the optical artificial neural network blood glucose detection chip containing different optical modulation structures, image sensors, and processors with different fully connected parameters and nonlinear activation parameters is trained, the different optical modulation structures are designed and implemented in a computer optical simulation design manner.

An embodiment of the present application also provides an optical artificial neural network intelligent agricultural precision control chip for agricultural precision control intelligent processing tasks, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; the incident light includes reflected light, transmitted light and/or radiated light of an agricultural object; and the agricultural object includes crops and/or soil;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer;

the processor is configured to perform fully connected processing and nonlinear activation processing on the electrical signals corresponding to the different location points to obtain agricultural precision control processing results; and the agricultural precision control intelligent processing tasks include one or more of detection of soil fertility, detection of pesticide spreading, detection of trace element content, detection of pesticide resistance, and detection of crop growth status; and the agricultural precision control processing results include one or more of detection results of soil fertility, detection results of pesticide spreading, detection results of trace element content, detection results of pesticide resistance, and detection results of crop growth status.

In an embodiment, the optical artificial neural network intelligent agricultural precision control chip includes a trained optical modulation structure, an image sensor and a processor;

the trained optical modulation structure, an image sensor and a processor refer to an optical modulation structure, an image sensor and an processor satisfying the training convergence condition obtained by training the optical artificial neural network intelligent agricultural precision control chip containing different optical modulation structures, image sensors, and processors with different fully connected parameters and different nonlinear activation parameters using input training samples and output training samples corresponding to agricultural precision control intelligent processing tasks;

in an embodiment, the input training samples include incident light reflected, transmitted and/or radiated by soils with different fertilities; the output training samples include corresponding soil fertilities; and/or, the input training samples include incident light reflected, transmitted and/or radiated by soils with different pesticide spreading conditions; the output training samples include corresponding pesticide spreading conditions; and/or, the input training samples include incident light reflected, transmitted and/or radiated by soils with different trace element content conditions; the output training samples include corresponding trace element content conditions; and/or, the input training samples include incident light reflected, transmitted and/or radiated by soils with different pesticide resistances; the output training samples include corresponding drug resistances; and/or, the input training samples include incident light reflected, transmitted and/or radiated by crops with different growth conditions; the output training samples include corresponding crop growth conditions.

In an embodiment, when the optical artificial neural network intelligent agricultural precision control chip containing different optical modulation structures, image sensors, and processors with different fully connected parameters and nonlinear activation parameters is trained, the different optical modulation structures are designed and implemented in a computer optical simulation design manner.

In an embodiment, the optical modulation structure in the optical filter layer includes a regular structure and/or an irregular structure; and/or, the optical modulation structure in the optical filter layer includes a discrete structure and/or a continuous structure.

In an embodiment, the optical filter layer has a single-layer structure or a multi-layer structure.

In an embodiment, the optical modulation structure in the optical filter layer includes a unit array composed of a plurality of micro-nano units, and each micro-nano unit corresponds to one or more pixels on the image sensor; each micro-nano unit has the same or different structure.

In an embodiment, the micro-nano unit includes a regular structure and/or an irregular structure; and/or the micro-nano unit includes a discrete structure and/or a continuous structure.

In an embodiment, the micro-nano unit includes a plurality of groups of micro-nano structure arrays, and each group of the micro-nano structure arrays has the same or different structure.

In an embodiment, each group of micro-nano structure array has broadband filtering or narrowband filtering functions.

In an embodiment, each group of micro-nano structure arrays is a periodic structure array or an aperiodic structure array.

In an embodiment, the plurality of groups of micro-nano structure arrays contained in the micro-nano unit has one or more groups of empty structures.

In an embodiment, the micro-nano unit has polarization-independent characteristics.

In an embodiment, the micro-nano unit has four-fold rotation symmetry.

In an embodiment, the optical filter layer is composed of one or more filter layers;

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

In an embodiment, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nanopillar two-dimensional materials, and nanowire two-dimensional materials.

In an embodiment, the optical filter layer has a thickness of $0.1\lambda$-$10\lambda$, where $\lambda$ represents the center wavelength of the incident light.

An embodiment of the present application also provides an intelligent agricultural control apparatus, including the optical artificial neural network intelligent agricultural precision control chip as described above.

An embodiment of the present application also provides a method for preparing the optical artificial neural network intelligent agricultural precision control chip as described above, including:

preparing an optical filter layer containing an optical modulation structure on a surface of a photosensitive area of an image sensor;

generating a processor with the functions of fully connected processing and nonlinear activation processing of signals; and connecting the image sensor and the processor;

wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light;

the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain agricultural precision control results; and the electrical signals are image signals modulated by the optical filter layer and the incident light includes reflected light, transmitted light and/or radiated light of an agricultural object; the agricultural object includes crops and/or soil.

In an embodiment, the method for preparing the optical artificial neural network intelligent agricultural precision control chip further includes a training process of the optical artificial neural network intelligent agricultural precision control chip and specifically includes:

training the optical artificial neural network intelligent agricultural precision control chip containing different optical modulation structures, image sensors, and processors with different fully connected parameters and different nonlinear activation parameters using input training samples and output training samples corresponding to the agricultural precision control intelligent processing tasks to obtain an optical modulation structure, an image sensor and an processor satisfying the training convergence condition and taking the optical modulation structure, the image sensor and the processor satisfying the training convergence condition as the trained optical modulation structure, the image sensor and the processor.

In an embodiment, when the optical artificial neural network intelligent agricultural precision control chip containing different optical modulation structures, image sensors, and processors with different fully connected parameters and nonlinear activation parameters is trained, the different optical modulation structures are designed and implemented in a computer optical simulation design manner.

An embodiment of the present application also provides an optical artificial neural network smelting endpoint monitoring chip for smelting endpoint monitoring tasks, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and the incident light includes reflected light, transmitted light and/or radiated light at a mouth of a steel-making furnace;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer; and the processor is configured to perform fully connected processing and nonlinear activation processing on the electrical signals corresponding to the different location points to obtain smelting endpoint monitoring results.

In an embodiment, the smelting endpoint monitoring tasks include recognition of the smelting endpoint, and the smelting endpoint monitoring result includes the smelting endpoint recognition result.

In an embodiment, the smelting endpoint monitoring tasks further include recognition of a carbon content and/or molten steel temperature during the smelting process, and the smelting endpoint monitoring result includes the carbon content and/or molten steel temperature recognition result during the smelting process.

In an embodiment, the optical artificial neural network smelting endpoint monitoring chip includes a trained optical modulation structure, an image sensor and a processor;

the trained optical modulation structure, an image sensor and a processor refer to an optical modulation structure, an image sensor and an processor satisfying the training convergence condition obtained by training the optical artificial neural network smelting endpoint monitoring chip containing different optical modulation structures, image sensors, and processors with different fully connected parameters and different nonlinear activation parameters using input training samples and output training samples corresponding to the smelting endpoint monitoring tasks; and the input training samples include incident light reflected, transmitted, and/or radiated at the mouth of the steel-making furnace when the smelting endpoint is arrived and when the smelting endpoint is not arrived; the output training samples include the determination result that whether the smelting endpoint is arrived.

In an embodiment, when the smelting endpoint monitoring task also includes recognition of a carbon content and/or molten steel temperature during the smelting process, correspondingly, the input training sample also includes incident light reflected, transmitted, and/or radiated at the mouth of the steel-making furnace when different carbon contents and/or molten steel temperature are obtained while smelting and the output training sample also includes the corresponding carbon content and/or molten steel temperature.

In an embodiment, when the optical artificial neural network smelting endpoint monitoring chip containing different optical modulation structures, image sensors, and processors with different fully connected parameters and nonlinear activation parameters is trained, the different optical modulation structures are designed and implemented in a computer optical simulation design manner.

In an embodiment, the optical modulation structure in the optical filter layer includes a regular structure and/or an irregular structure; and/or, the optical modulation structure in the optical filter layer includes a discrete structure and/or a continuous structure.

In an embodiment, the optical filter layer has a single-layer structure or a multi-layer structure.

In an embodiment, the optical modulation structure in the optical filter layer includes a unit array composed of a plurality of micro-nano units, and each micro-nano unit corresponds to one or more pixels on the image sensor; each micro-nano unit has the same or different structure.

In an embodiment, the micro-nano unit includes a regular structure and/or an irregular structure; and/or the micro-nano unit includes a discrete structure and/or a continuous structure.

In an embodiment, the micro-nano unit includes a plurality of groups of micro-nano structure arrays, and each group of the micro-nano structure arrays has the same or different structure.

In an embodiment, each group of micro-nano structure array has broadband filtering or narrowband filtering functions.

In an embodiment, each group of micro-nano structure arrays is a periodic structure array or an aperiodic structure array.

In an embodiment, the plurality of groups of micro-nano structure arrays contained in the micro-nano unit has one or more groups of empty structures.

In an embodiment, the micro-nano unit has polarization-independent characteristics.

In an embodiment, the micro-nano unit has four-fold rotation symmetry.

In an embodiment, the optical filter layer is composed of one or more filter layers;

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

In an embodiment, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nanopillar two-dimensional materials, and nanowire two-dimensional materials.

In an embodiment, the optical filter layer has a thickness of $0.1\lambda$-$10\lambda$, where $\lambda$ represents the center wavelength of the incident light.

An embodiment of the present application also provides an intelligent smelting control apparatus, including the optical artificial neural network smelting endpoint monitoring chip as described above.

An embodiment of the present application also provides a method for preparing the optical artificial neural network smelting endpoint monitoring chip as described above, including:
preparing an optical filter layer containing an optical modulation structure on a surface of a photosensitive area of an image sensor;
generating a processor with the functions of fully connected processing and nonlinear activation processing of signals; and
connecting the image sensor and the processor;
wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light;
the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain smelting endpoint monitoring results; and the electrical signals are image signals modulated by the optical filter layer and the incident light includes reflected light, transmitted light and/or radiated light at a mouth of a steel-making furnace.

In an embodiment, the method for preparing the optical artificial neural network smelting endpoint monitoring chip further includes a training process of the optical artificial neural network smelting endpoint monitoring chip and specifically includes:
training the optical artificial neural network smelting endpoint monitoring chip containing different optical modulation structures, image sensors, and processors with different fully connected parameters and different nonlinear activation parameters using input training samples and output training samples corresponding to the smelting endpoint monitoring tasks to obtain an optical modulation structure, an image sensor and an processor satisfying the training convergence condition and taking the optical modulation structure, the image sensor and the processor satisfying the training convergence condition as the trained optical modulation structure, the image sensor and the processor.

In an embodiment, when the optical artificial neural network smelting endpoint monitoring chip containing different optical modulation structures, image sensors, and processors with different fully connected parameters and nonlinear activation parameters is trained, the different optical modulation structures are designed and implemented in a computer optical simulation design manner.

For the optical artificial neural network intelligent chip, the preparation method thereof and the intelligent processing apparatus provided by the embodiments of the present application, a new intelligent chip capable of implementing the artificial neural network function is provided in which the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area through the optical modulation structure. Accordingly, the image sensor is configured to convert the information carried in the incident light corresponding to different location points after being modulated by the optical filter layer into electric signals corresponding to the different location points, and at the same time, the processor connected with the image sensor is configured to perform fully connected processing and nonlinear activation processing on the electrical signals corresponding to the different location points to obtain output signals of the artificial neural network. It can be seen that in the intelligent chip, the optical filter layer serves as the input layer of the artificial neural network, the image sensor serves as the linear layer of the artificial neural network. At the same time, the filtering effect of the optical filter layer on the incident light entering the optical filter layer corresponds to the connection weight from the input layer to the linear layer, that is, the optical filter layer and the image sensor of the intelligent chip provide related functions of the input layer and the linear layer in the artificial neural network. That is, in the embodiments of the present application, the input layer and the linear layer in the artificial neural network implemented by software are peeled apart and the two-layer structure of the input layer and the linear layer in the artificial neural network is implemented by hardware, so that no complicated signal processing and algorithm processing corresponding to the input layer and the linear layer need to be performed in the subsequent artificial neural network intelligent processing using the intelligent chip and the processor in the intelligent chip only needs to perform fully connected processing and nonlinear activation processing on the electrical signals, which may greatly reduce the power consumption and delay of artificial neural network processing. It can be seen that in the embodiments of the present application, the optical filter layer serves as the input layer of the artificial neural network, the image sensor serves as the linear layer of the artificial neural network, the filtering effect of the optical filter layer on the incident light entering the optical filter layer serves as the connection weight from the input layer to the linear layer; information carried in the incident light of the target object is projected into electrical signals using the optical filter layer and the image sensor and the fully connected processing and nonlinear activation processing on the electrical signals are then implemented in the processor. Also, in the embodiment of the present application, the complicated signal processing and algorithm processing corresponding to the input layer and linear layer may not only be omitted and the image information of the target object, spectral information, angle information of the incident light and phase information of the incident light, that is, the information carried by the incident light at different points in the target object space may but also actually simultaneously utilized. Since the information carried by the incident light at different points in the target object space covers information of the target object such as images, composition, shape, three-dimensional depth, structure and the like, the information of the target object such as images, composition, shape, three-dimensional depth, structure and the like is covered when the recognition processing is performed according to the information carried by the incident light at different points in the target object space, so as to solve the problem mentioned in the Background that it is difficult to ensure the accuracy of recognition using only the two-dimensional image information of the target objects, for example, it is difficult to distinguish between real faces and photos of faces. In the optical artificial neural network chip provided by the embodiment of the present application, not only the effect of low power consumption and low latency and but also the effect of high accuracy may be provided, so that it may be prepared for intelligent processing tasks such as intelligent perception, intelligent recognition and/or intelligent decision.

BRIEF DESCRIPTION OF THE DRAWINGS

In order to more clearly illustrate technical solutions disclosed in certain embodiments of the present application, the drawings aiding in the descriptions of the embodiments be briefly described below. Obviously, the drawings in the following description only show certain embodiments of the present application, and other drawings can be obtained according to the drawings without any creative work for those skilled in the art.

DETAILED DESCRIPTION

Figure 1:
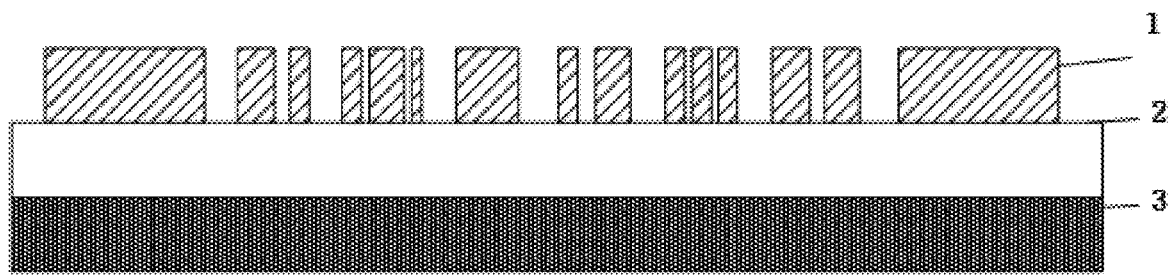
FIG. 1 is a schematic structural diagram of an optical artificial neural network intelligent chip according to a first exemplary embodiment of the present application.

In order to illustrate the objectives, technical solutions and advantages of the embodiments of the present application clearly, the technical solutions in the embodiments of the present application will be described clearly and completely in conjunction with the companying drawings in the embodiments of the present application. Obviously, the described embodiments are part of the embodiments of the present application, rather than all of the embodiments. All other embodiments obtained by a person of ordinary skill in the art based on the embodiments of the present application without any creative effort fall within the protection scope of the present application.

Traditional intelligent recognition technologies are to recognize people or objects usually by imaging people or objects firstly, and then performing steps of image preprocessing, feature extraction, feature matching, etc. However, it is difficult to ensure the accuracy of recognition using only the two-dimensional image information of people or objects, for example, it is difficult to distinguish between real faces and photos of faces. Also, during the imaging process, optical information needs to be converted into digital electronic signals, and then transmitted to a computer for subsequent algorithm processing. Therefore, the transmission and processing of a large amount of data causes greater power consumption and delay. On this basis, an embodiment of the present application provides an optical artificial neural network intelligent chip in which an optical filter layer corresponds to an input layer of the artificial neural network, an image sensor corresponds to a linear layer of the artificial neural network, and the filtering effect of the optical filter layer on incident light entering the optical filter layer corresponds to the connection weight from the input layer to the linear layer. In the embodiment of the present application, spatial spectrum information of a target object is projected into electrical signals using the optical filter layer and the image sensor and the fully connected processing and non-linear activation processing on the electrical signals are then implemented in the processor. Through the embodiment of the present application, not only the complicated signal processing and algorithm processing corresponding to the input layer and linear layer may be omitted, and the light intensity distribution information (i.e., image information) of the target object, spectral information, angle of incident light and phase information of incident light, that is, the information carried by the incident light at different points in the target object space may also be actually simultaneously utilized and thus the accuracy of intelligent processing (such as intelligent recognition) may be improved using the spatial image, spectral information, angle information and phase information. Therefore, through the optical artificial neural network chip according to the embodiment of the present application, not only the effects of low power consumption and low delay may be realized, but also the accuracy of intelligent processing may be improved, so that it may be better applied in intelligent processing fields such as intelligent perception, intelligent recognition and/or intelligent decision-making. The content according to the present application will be explained and described in detail below through specific embodiments.

As shown in FIG. 1, a first embodiment of the present application provides an optical artificial neural network intelligent chip, including: an optical filter layer 1, an image sensor 2, and a processor 3; the optical filter layer 1 corresponds to an input layer and a connection weight from the input layer to a linear layer of an artificial neural network; the image sensor 2 corresponds to the linear layer of the artificial neural network; and the processor 3 corresponds to a nonlinear layer and an output layer of the artificial neural network;

the optical filter layer 1 is disposed on the surface of a photosensitive area of the image sensor, the optical filter layer 1 includes an optical modulation structure, and is configured to modulate with different spectra of which the intensity changes as a wavelength changes, that is, modulate under different intensities, incident light which is incident to different location points of the optical modulation structure, respectively to obtain information carried in the incident light corresponding to different location points on the surface of the photosensitive area; the information carried in the incident light includes light intensity distribution information, spectral information, angle information of the incident light and phase information of the incident light;

the image sensor 2 is configured to convert information carried in the incident light corresponding to different location points after being modulated by the optical filter layer 1 into electric signals corresponding to the different location points, and send the electric signals corresponding to the different location points to the processor 3 and the electrical signals are image signals modulated by the optical filter layer; and the processor 3 is configured to perform fully connected processing and nonlinear activation processing on the electrical signals corresponding to the different location points to obtain output signals of the artificial neural network.

In this embodiment, the optical filter layer 1 is disposed on the surface of a photosensitive area of the image sensor, the optical filter layer 1 includes an optical modulation structure, and is configured to modulate, with different spectra, incident light which is incident to different location points of the optical modulation structure respectively by the optical modulation structure, through the optical modulation structure to obtain information carried in the incident light corresponding to different location points on the surface of the photosensitive area. The image sensor 2 is configured to convert information carried in the incident light corresponding to different location points into electric signals corresponding to the different location points, i.e., image signals modulated by the optical filter layer, and at the same time, the processor 3 is configured to perform fully connected processing and nonlinear activation processing on the electrical signals corresponding to the different location points to obtain output signals of the artificial neural network.

In this embodiment, the optical filter layer 1 includes an optical modulation structure, through which incident light (correlated acting light such as reflected light, transmitted light, radiated light, etc. of the target to be recognized) entering into different location points of the optical modulation structure is modulated under spectra of different intensities to obtain information carried by the incident light corresponding to different location points on the surface of the photosensitive area of the image sensor 2.

In this embodiment, it may be understood that the modulation intensity is related to the specific structure form of the optical modulation structure. For example, different modulation intensities may be provided by designing different optical modulation structures (such as changing the shape and/or size parameters of the optical modulation structure).

In this embodiment, it may be understood that the optical modulation structures at different location points of the optical filter layer 1 have different spectral modulation effects on the incident light, and the modulation intensity of the optical modulation structure to the different wavelength components of the incident light corresponds to the connection strength of the artificial neural network, that is, the corresponding input layer and the connection weight from the input layer to the linear layer. It should be noted that the optical filter layer 1 is composed of multiple optical filter units, and the optical modulation structures at different positions in each optical filter unit are different, so they have different spectrum modulation effects on the incident light. The optical modulation structure at different positions between the optical filter units may be the same or different, and have the same or different spectrum modulation effects on the incident light.

In this embodiment, the image sensor 2 converts information carried by the incident light corresponding to different location points into electrical signals corresponding to the different location points, and sends the electrical signals corresponding to the different location points to the processor 3, and the image sensor 2 corresponds to the linear layer of the neural network.

In this embodiment, the processor 3 performs fully connected processing and nonlinear activation processing on the electrical signals corresponding to the different location points to obtain output signals of the artificial neural network.

It can be understood that the processor 3 corresponds to a nonlinear layer and the output layer of the neural network, and it can also be understood that it corresponds to the remaining layers (all other layers) except the input layer and the linear layer in the neural network.

In addition, it needs to be supplemented that the processor 3 may be provided inside the intelligent chip, that is, the processor 3 may be provided inside the intelligent chip together with the optical filter layer 1 and the image sensor 2, or separately arranged outside the intelligent chip and connected to the image sensor 2 inside the intelligent chip through a data cable or a connection device, which is not limited in this embodiment.

In addition, it should be noted that the processor 3 may be implemented by a computer, an ARM or FPGA circuit board with a certain computing capability, or a microprocessor, which is not limited in this embodiment. In addition, as mentioned above, the processor 3 may be integrated in the intelligent chip, or may be independently disposed outside the intelligent chip. When the processor 3 is independently disposed outside the intelligent chip, the electrical signals in the image sensor 2 may be read out to the processor 3 through a signal readout circuit, and the processor 3 performs fully connected processing and nonlinear activation processing on the read electrical signals.

In this embodiment, it can be understood that when the processor 3 performs nonlinear activation processing, it can be implemented by using a nonlinear activation function, for example, a Sigmoid function, a Tanh function, a ReLU function, etc., which is not limited in this embodiment.

In this embodiment, the optical filter layer 1 corresponds to the input layer of the artificial neural network and the connection weight from the input layer to the linear layer, and the image sensor 2 corresponds to the linear layer of the artificial neural network, converts information carried by incident light at different location points in a space into electrical signals, the processor 3 corresponds to the nonlinear layer and the output layer of the artificial neural network, fully connects the electrical signals at different location points and obtains the output signal of the artificial neural network through the nonlinear activation function, thereby providing intelligent perception, intelligent recognition and/or intelligent decision of specific targets.

Figure 2:
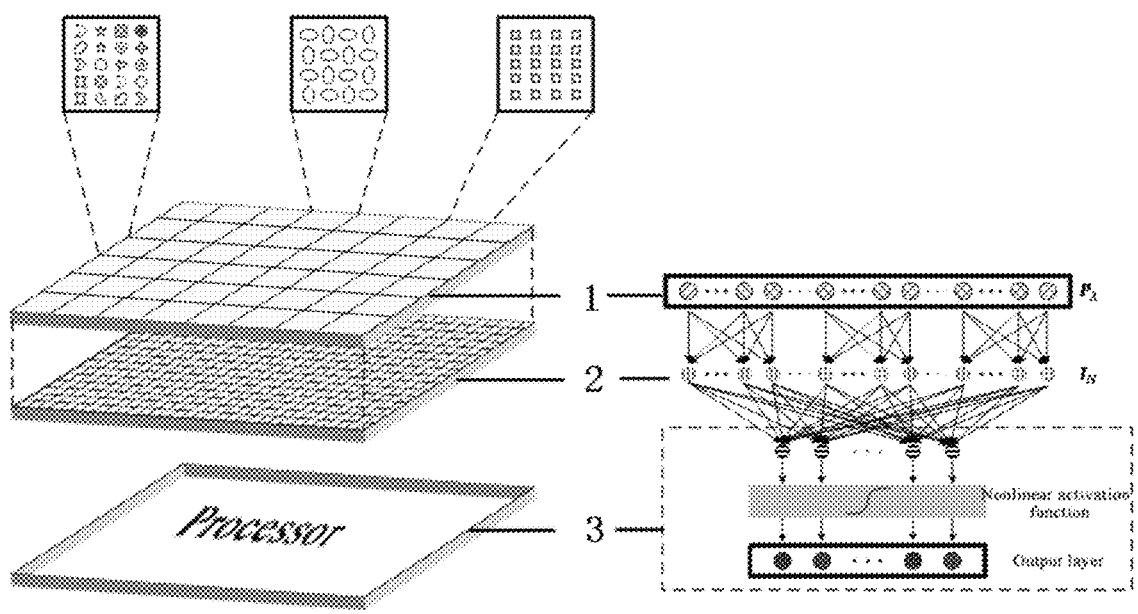
FIG. 2 is a schematic diagram of a recognition principle of an optical artificial neural network intelligent chip according to an exemplary embodiment of the present application.

As shown on the left side of FIG. 2, the optical artificial neural network intelligent chip includes an optical filter layer 1, an image sensor 2 and a processor 3. In FIG. 2, the processor 3 is provided by a signal readout circuit and a computer. As shown on the right side of FIG. 2, the optical filter layer 1 in the optical artificial neural network intelligent chip corresponds to the input layer of the artificial neural network, the image sensor 2 corresponds to the linear layer of the artificial neural network, and the processor 3 corresponds to the nonlinear layer and the output layer of the artificial neural network, and the filtering effect of the optical filter layer 1 on the incident light entering the optical filter layer 1 corresponds to the connection weight from the input layer to the linear layer. The optical filter layer and the image sensor in the intelligent chip provided in this embodiment realizes the related functions of the input layer and the linear layer in the artificial neural network through hardware, so that no complicated signal processing and algorithm processing corresponding to the input layer and the linear layer need to be performed in the subsequent artificial neural network intelligent processing using the intelligent chip, which may greatly reduce the power consumption and delay of artificial neural network processing. In addition, since the image information of the target object, image information at different points in the space, spectral information, angle information of the incident light and phase information of the incident light are simultaneously utilized in this embodiment, the intelligent processing of the target object may be realized more accurately.

As shown on the right side of FIG. 2, the incident light frequency spectrum $P_\lambda$ at different positions of the optical filter layer 1 is projected/connected to the photocurrent response $I_N$ of the image sensor. The processor 3 includes a signal readout circuit and a computer. The signal readout circuit in the processor 3 is configured to read and transmit the photocurrent response to the computer, and the computer is configured to perform fully connected processing and nonlinear activation processing on the electrical signal, and finally output the results.

Figure 3:
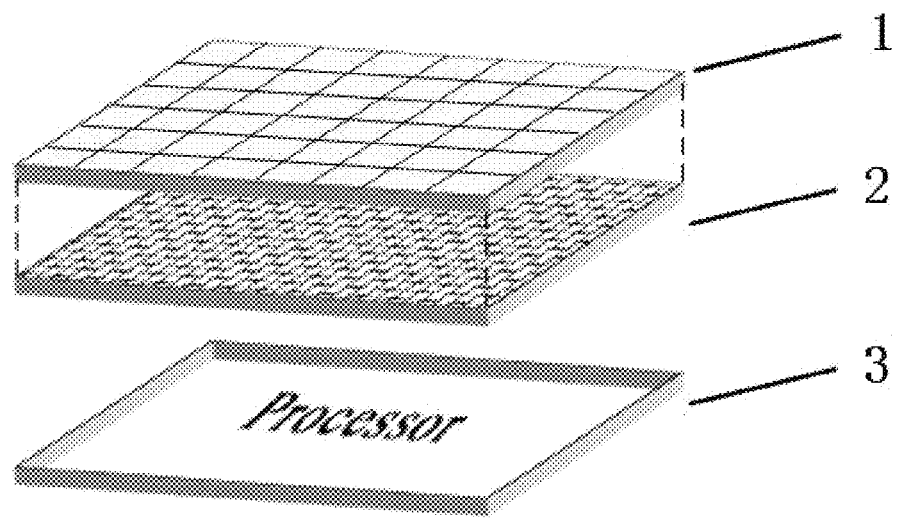
FIG. 3 is a schematic diagram of disassembling an optical artificial neural network intelligent chip according to an exemplary embodiment of the present application.

As shown in FIG. 3, the optical modulation structure of the optical filter layer 1 is integrated above the image sensor 2 to modulate the incident light, and projects/connects frequency-spectrum information of the incident light to different pixels of the image sensor 2, and obtain electrical signal containing the frequency-spectrum information of the incident light and image information, that is, after the incident light passes through the optical filter layer 1, it is converted into an electrical signal by the image sensor 2 to form an image containing the frequency-spectrum information of the incident light, and finally the processor 3 connected with the image sensor 2 processes the electrical signal containing the frequency-spectrum information of the incident light and image information. In the optical artificial neural network chip according to the embodiment of the present application, the image information of the target object, spectral information, angle information of the incident light and phase information of the incident light, that is, the information carried by the incident light at different points in the target object space may actually simultaneously utilized. Since the information carried by the incident light at different points in the target object space covers information of the target object such as images, composition, shape, three-dimensional depth, structure and the like, the information of the target object such as images, composition, shape, three-dimensional depth, structure and the like is covered when the recognition processing is performed according to the information carried by the incident light at different points in the target object space, so as to solve the problem mentioned in the Background that it is difficult to ensure the accuracy of recognition using only the two-dimensional image information of the target objects, for example, it is difficult to distinguish between real faces and photos of faces. intelligent perception, intelligent recognition and/or intelligent decision functions for different application fields are provided, and a spectrum optical artificial neural network intelligent chip with low power consumption, low latency and high accuracy is provided.

The optical artificial neural network intelligent chip provided by the embodiment of the present application includes the optical filter layer, the image sensor, and the processor, wherein the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area through the optical modulation structure. Accordingly, the image sensor is configured to convert the information carried in the incident light corresponding to different location points after being modulated by the optical filter layer into electric signals corresponding to the different location points, and at the same time, the processor connected with the image sensor is configured to perform fully connected processing and nonlinear activation processing on the electrical signals corresponding to the different location points to obtain output signals of the artificial neural network. It can be seen that in the intelligent chip, the optical filter layer serves as the input layer of the artificial neural network, the image sensor serves as the linear layer of the artificial neural network. At the same time, the filtering effect of the optical filter layer on the incident light entering the optical filter layer corresponds to the connection weight from the input layer to the linear layer, that is, the optical filter layer and the image sensor of the intelligent chip provide related functions of the input layer and the linear layer in the artificial neural network. That is, in the embodiment of the present application, the input layer and the linear layer in the artificial neural network implemented by software are stripped and the two-layer structure of the input layer and the linear layer in the artificial neural network is implemented by hardware, so that no complicated signal processing and algorithm processing corresponding to the input layer and the linear layer need to be performed in the subsequent artificial neural network intelligent processing using the intelligent chip and the processor in the intelligent chip only needs to perform fully connected processing and nonlinear activation processing on the electrical signals, which may greatly reduce the power consumption and delay of artificial neural network processing. It can be seen that in the embodiment of the present application, the optical filter layer serves as the input layer of the artificial neural network, the image sensor serves as the linear layer of the artificial neural network, the filtering effect of the optical filter layer on the incident light entering the optical filter layer serves as the connection weight from the input layer to the linear layer; information carried in the incident light of the target object is projected into electrical signals using the optical filter layer and the image sensor and the fully connected processing and nonlinear activation processing on the electrical signals are then implemented in the processor. Also, in the embodiment of the present application, the complicated signal processing and algorithm processing corresponding to the input layer and linear layer may not only be omitted and the image information of the target object, spectral information, angle information of the incident light and phase information of the incident light, that is, the information carried by the incident light at different points in the target object space may but also actually simultaneously utilized. Since the information carried by the incident light at different points in the target object space covers information of the target object such as images, composition, shape, three-dimensional depth, structure and the like, the information of the target object such as images, composition, shape, three-dimensional depth, structure and the like is covered when the recognition processing is performed according to the information carried by the incident light at different points in the target object space, so as to solve the problem mentioned in the Background that it is difficult to ensure the accuracy of recognition using only the two-dimensional image information of the target objects, for example, it is difficult to distinguish between real faces and photos of faces. In the optical artificial neural network chip provided by the embodiment of the present application, not only the effect of low power consumption and low latency and but also the effect of high accuracy may be provided, so that it may be prepared for intelligent processing tasks such as intelligent perception, intelligent recognition and/or intelligent decision.

Based on the content of the foregoing embodiments, in an embodiment, the optical artificial neural network intelligent chip is used for intelligent processing tasks of a target object; the intelligent processing tasks include at least one or more of an intelligent perception task, an intelligent recognition task and an intelligent decision task;

reflected light, transmitted light and/or radiation light of the target object enters a trained optical artificial neural network intelligent chip to obtain intelligent processing results of the target object; the intelligent processing results include at least one or more of an intelligent perception result, an intelligent recognition result and/or an intelligent decision result; and the trained optical artificial neural network intelligent chip refers to an optical artificial neural network intelligent chip including a trained optical modulation structure, an image sensor and a processor; the trained optical modulation structure, image sensor and processor refer to an optical modulation structure, an image sensor and an processor satisfying a training convergence condition obtained by training the optical artificial neural network intelligent chip containing different optical modulation structures, image sensors, and processors with different fully connected parameters and nonlinear activation parameters using input training samples and output training samples corresponding to the intelligent processing task.

In this embodiment, the optical artificial neural network intelligent chip may be used for intelligent processing tasks of a target object, for example, including at least one or more of an intelligent perception task, an intelligent recognition task and an intelligent decision task.

In this embodiment, it may be understood that intelligent perception refers to mapping signals of the physical world to digital information through hardware devices such as cameras, microphones or other sensors, and with the help of frontier technologies such as voice recognition and image recognition, and then further promoting this digital information to a perceptible level, such as memory, comprehension, planning, decision-making, and so on. Intelligent recognition refers to a technology for processing, analyzing and understanding images using computers to recognize various targets and objects in different modes. At this stage, the intelligent recognition technology is generally divided into face recognition and commodity recognition. Face recognition is mainly used in security inspections, identity verification and mobile payment while commodity recognition is mainly used in the commodity circulation process, especially in unmanned retail fields such as unmanned shelves and intelligent retail cabinets. Intelligent decision-making refers to automatically organizing and coordinating the operation of multiple models by a computer, accessing and processing data in a large number of databases, and performing corresponding data processing and numerical calculations.

In this embodiment, the reflected light, transmitted light and/or radiated light of the target object enters the trained optical artificial neural network intelligent chip to obtain the intelligent processing result of the target object.

In this embodiment, recognition tasks of the target object are taken as an example for description. It may be understood that when the intelligent chip is used for the recognition task, the optical artificial neural network intelligent chip needs to be trained first. Here, the training the optical artificial neural network intelligent chip refers to determining an optical modulation structure suitable for a current recognition task, as well as the fully connected parameters and the nonlinear activation parameters suitable for the current recognition task through training.

It may be understood that since the filtering effect of the optical filter layer on the incident light entering the optical filter layer corresponds to the connection weight from the input layer to the linear layer of the artificial neural network, changing the optical modulation structure in the optical filter layer during training corresponds to changing the connection weight from the input layer to the linear layer of the artificial neural network. Through training the convergence conditions, the optical modulation structure suitable for the current recognition task, as well as the fully connected parameters and the nonlinear activation parameters suitable for the current recognition task are determined so that the training of the intelligent chip is completed.

It may be understood that after the intelligent chip is trained, the intelligent chip may be employed to perform recognition tasks. Specifically, after the incident light carrying the image information of the target object and the spatial spectrum information enters the optical filter layer 1 of the trained intelligent chip, the optical modulation structure in the optical filter layer 1 modulates the incident light, and the intensity of the modulated light signal is detected by the image sensor 2 and converted into an electrical signal, and then the processor 3 performs fully connected processing and nonlinear activation processing on electrical signal to obtain the recognition result of the target object.

Figure 4:
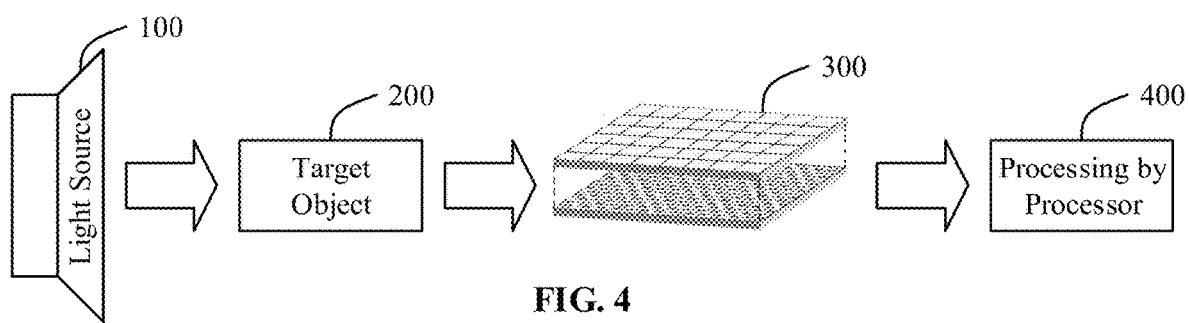
FIG. 4 is a schematic diagram of a target object recognition process according to an exemplary embodiment of the present application.

As shown in FIG. 4, the complete process for recognition of the target object includes: allowing a broad-spectrum light source 100 to illuminate the target object 200, and then collecting the reflected or transmitted light of the target object by the optical artificial neural network intelligent chip 300, or collecting light radiated directly and externally by the target object 200 by the optical artificial neural network intelligent chip 300 and processing the radiated light by the optical filter layer, the image sensor and the processor in the intelligent chip to obtain the recognition result.

In an embodiment, the trained optical artificial neural network intelligent chip refers to an optical artificial neural network intelligent chip including a trained optical modulation structure, an image sensor and a processor; the trained optical modulation structure, the image sensor and the processor refer to an optical modulation structure, an image sensor and an processor satisfying a training convergence condition obtained by training the optical artificial neural network intelligent chip containing different optical modulation structures, image sensors, and processors with different fully connected parameters and nonlinear activation parameters using input training samples and output training samples corresponding to the intelligent processing task.

For example, for an intelligent recognition task, an input training sample corresponding to the intelligent recognition task is a sample of the object to be recognized, and an output training sample corresponding to the intelligent recognition task is the recognition result of the sample of the object to be recognized. It may be understood that for the recognition task, the advantage of the intelligent chip provided in this embodiment is that the spatial spectrum information of the object to be recognized may be obtained. Therefore, in order to make full use of this advantage, the sample of the object to be recognized as the input training sample preferably adopts real recognition objects rather than two-dimensional images of the object to be recognized. Of course, this does not mean that a two-dimensional image cannot be used as a sample of the object to be recognized.

In addition, the optical artificial neural network intelligent chip provided in this embodiment can also be used for other intelligent processing tasks of the target object, such as intelligent perception and intelligent decision-making.

In this embodiment, the optical filter layer 1 serves as the input layer of the neural network, and the image sensor 2 serves as the linear layer of the neural network. In order to minimize a loss function of the neural network, the modulation intensity of the optical modulation structure for different wavelength components in the incident light of the target object serves as the connection weight from the input layer to the linear layer of the neural network. The modulation intensity of different wavelength components in the incident light of the target object may be adjusted by adjusting the structure of the filter, so as to adjust the connection weight from the input layer to the linear layer to further optimize the training of the neural network.

Therefore, the optical modulation structure in this embodiment is obtained based on training the neural network, the training sample is optically simulated by a computer to obtain a sample modulation intensity of the optical modulation structure in the training sample for the different wavelength components in the incident light of the target object among the intelligent processing task. The sample modulation intensity serves as the connection weight from the input layer to the linear layer of the neural network, nonlinear activation is performed and the neural network is trained using the training samples corresponding to the intelligent processing task until the neural network converges, and the optical modulation structure corresponding to the training sample serves as the optical filter layer corresponding to the intelligent processing task.

In the embodiment of the present application, by implementing the input layer (optical filter layer) and linear layer (image sensor) of the neural network in the physical layer, not only the complicated signal processing and algorithm processing corresponding to the input layer and linear layer may be omitted, and the image information of the target object, spectral information, angle information of the incident light and phase information of the incident light, that is, the information carried by the incident light at different points in the target object space, may also be actually simultaneously utilized. Since the information carried by the incident light at different points in the target object space covers information of the target object such as images, composition, shape, three-dimensional depth, structure and the like, the information of the target object such as images, composition, shape, three-dimensional depth, structure and the like is covered when the recognition processing is performed according to the information carried by the incident light at different points in the target object space, so as to solve the problem mentioned in the Background that it is difficult to ensure the accuracy of recognition using only the two-dimensional image information of the target objects, for example, it is difficult to distinguish between real faces and photos of faces. In the optical artificial neural network chip provided by the embodiment of the present application, not only the effect of low power consumption and low latency and but also the effect of high accuracy may be provided, so that it may be prepared for intelligent processing tasks such as intelligent perception, intelligent recognition and/or intelligent decision.

Based on the content of the foregoing embodiments, in an embodiment, when the optical artificial neural network intelligent chip containing different optical modulation structures, image sensors, and processors with different fully connected parameters and nonlinear activation parameters is trained, the different optical modulation structures are designed and implemented in a computer optical simulation design manner.

In this embodiment, optical simulation may allow users to experience a product through a digital environment before making physical prototypes. For example, for cars, appropriate optical simulation solutions can not only effectively help users improve design efficiency, but also simulate the interaction of light and materials in order to know the display effect of the product under real conditions because the illumination and reflected light will interfere with the driver's attention, especially when driving at night. Therefore, in this embodiment, the optical modulation structure is designed through computer optical simulation, and the optical modulation structure is adjusted through optical simulation until the neural network converges, it is determined that the corresponding optical modulation structure is the size of the optical modulation structure that needs to be produced finally, thereby saving prototype production time and cost, improving product efficiency, and easily solving complex optical problems.

For example, the optical modulation structure may be simulated and designed by a FDTD software, and the optical modulation structure may be changed in the optical simulation, so that the modulation intensity of the optical modulation structure for different incident lights may be accurately predicted, and may serve as the connection weight from the input layer and the linear layer of the neural network to train the optical artificial neural network intelligent chip, so as to accurately obtain the optical modulation structure.

In this embodiment, the optical modulation structure is designed by adopting a computer optical simulation design manner, which saves prototype production time and cost, and improves the product efficiency.

Based on the content of the foregoing embodiments, in an embodiment, the optical modulation structure in the optical filter layer includes a regular structure and/or an irregular structure; and/or, the optical modulation structure in the optical filter layer includes a discrete structure and/or a continuous structure.

In this embodiment, the optical modulation structure in the optical filter layer may include only a regular structure, or only an irregular structure, or may include both a regular structure and an irregular structure.

In this embodiment, the optical modulation structure including a regular structure may mean that the smallest modulation units included in the optical modulation structure have a regular structure, for example, the smallest modulation units may have regular shapes such as rectangles, squares, and circles. In addition, the optical modulation structure including a regular structure here may also mean that the smallest modulation units included in the optical modulation structure are regularly arranged, for example, arranged in a regular array form, a circular form, a trapezoidal form, a polygonal form, etc. In addition, the optical modulation structure including a regular structure may also mean that the smallest modulation units included in the optical modulation structure have a regular structure, and at the same time the smallest modulation units are regularly arranged.

In this embodiment, the optical modulation structure including an irregular structure may mean that the smallest modulation units included in the optical modulation structure have an irregular structure, for example, the smallest modulation units may have regular shapes such as irregular polygons, random shapes, etc. In addition, the optical modulation structure including an irregular structure here may also mean that the smallest modulation units included in the optical modulation structure are irregularly arranged, for example, arranged in an irregular polygonal form, a random arrangement form, etc. In addition, the optical modulation structure including an irregular structure may also mean that the smallest modulation units included in the optical modulation structure have an irregular structure, and at the same time the smallest modulation units are irregularly arranged.

In this embodiment, the optical modulation structure in the optical filter layer may include a discrete structure, may also include a continuous structure, or may include both a discrete structure and a continuous structure.

In this embodiment, the optical modulation structure including a continuous structure may mean that the optical modulation structure is composed of continuous modulation patterns; the optical modulation structure including a discrete structure here may mean that the optical modulation structure is composed of discrete modulation patterns.

It may be understood that the continuous modulation pattern here may refer to a linear pattern, a wavy line pattern, a zigzag line pattern, and the like.

It may be understood that the discrete modulation pattern here may refer to a modulation pattern formed by discrete shapes (such as discrete points, discrete triangles, discrete stars).

In this embodiment, it should be noted that the optical modulation structure has different modulation effects on light of different wavelengths, and specific modulation methods include, but are not limited to, scattering, absorption, interference, surface plasmons, resonance enhancement, and the like. By designing different filter structures, the corresponding transmission spectra are different after light passes through different groups of filter structures.

Based on the content of the foregoing embodiments, in an embodiment, the optical filter layer has a single-layer structure or a multilayer structure.

In this embodiment, it should be noted that the optical filter layer may have a single-layer filter structure or a multilayer filter structure, for example, a two-layer, three-layer, or four-layer structure.

In this embodiment, as shown in FIG. 1, the optical filter layer 1 has a single-layer structure, and the thickness of the optical filter layer 1 is related to the target wavelength range.

For a wavelength of 400 nm to 10 µm, the grating structure may have a thickness of 50 nm to 5 µm.

It may be understood that since the optical filter layer 1 has the role of modulating the incident light, it is preferably made of materials with high refractive index and low loss. For example, silicon, germanium, silicon germanium materials, silicon compounds, germanium compounds, III-V family materials may be selected for preparing the optical filter layer. The silicon compounds include, but are not limited to, silicon nitride, silicon dioxide, silicon carbide.

In addition, it should be noted that, in order to form more or more complex connection weights from the input layer to the linear layer, the optical filter layer 1 may be preferably configured as a multilayer structure, and optical modulation structure corresponding to each layer may be set to different structures, thereby increasing the spectral modulation capability of the optical filter layer to incident light, forming more or more complex connection weights from the input layer to the linear layer, and further improving the accuracy when the intelligent chip performs the intelligent tasks.

In addition, it should be noted that for a filter layer including a multilayer structure, each layer structure may be made of the same or different materials. For example, for a two-layer optical filter layer 1, the first layer may be a silicon layer, and the second layer may be a silicon nitride layer.

It should be noted that the thickness of the optical filter layer 1 is related to the target wavelength range. For a wavelength of 400 nm to 10 µm, the multilayer structure may have a total thickness of 50 nm to 5 µm.

Based on the content of the foregoing embodiments, in an embodiment, the optical modulation structure in the optical filter layer includes a unit array composed of a plurality of micro-nano units, and each micro-nano unit corresponds to one or more pixels on the image sensor; each micro-nano unit has the same or different structure.

In this embodiment, in order to obtain the connection weights distributed in an array (configured to connect the connection weights between the input layer and the linear layer) so that the processor may perform subsequent fully connected and nonlinear activation processing, it is preferable in this embodiment that the optical modulation structure is in the form of an array structure. Specifically, the optical modulation structure includes a unit array composed of a plurality of micro-nano units, and each micro-nano unit corresponds to one or more pixels on the image sensor. It should be noted that each micro-nano unit has the same or different structure. In addition, it should be noted that each micro-nano unit has may have periodic or aperiodic structures. In addition, it should be noted that each micro-nano unit may further include a plurality of groups of micro-nano structure arrays, and each group of the micro-nano structure arrays has the same or different structure.

Figure 5:
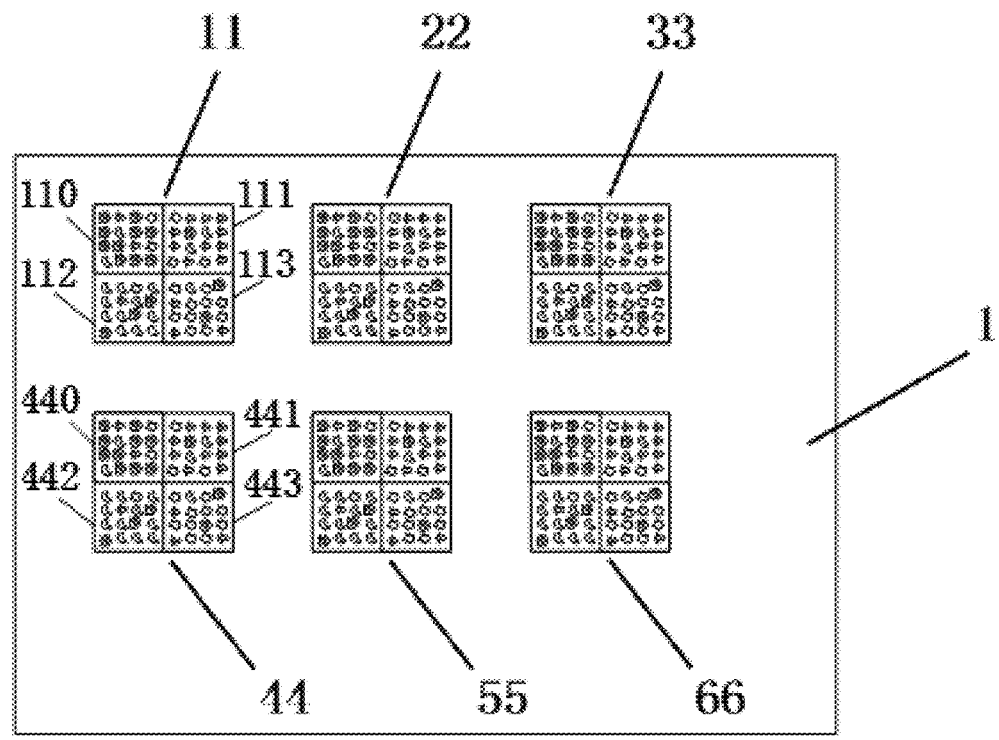
FIG. 5 is a top view of an optical filter layer according to an exemplary embodiment of the present application.
Figure 6:
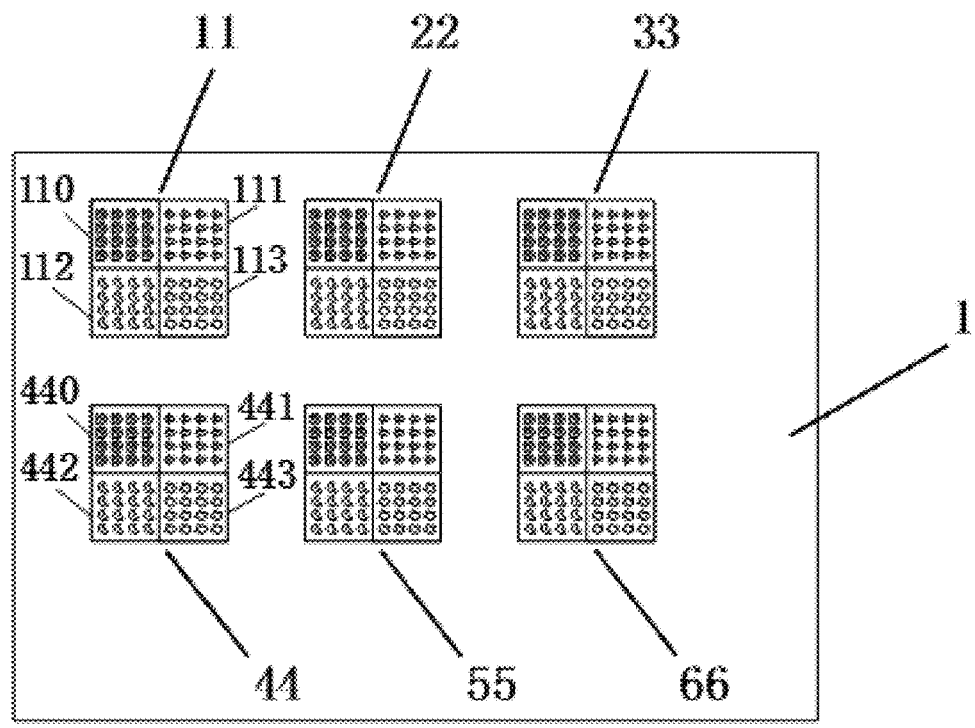
FIG. 6 is a top view of another optical filter layer according to an exemplary embodiment of the present application.
Figure 7:
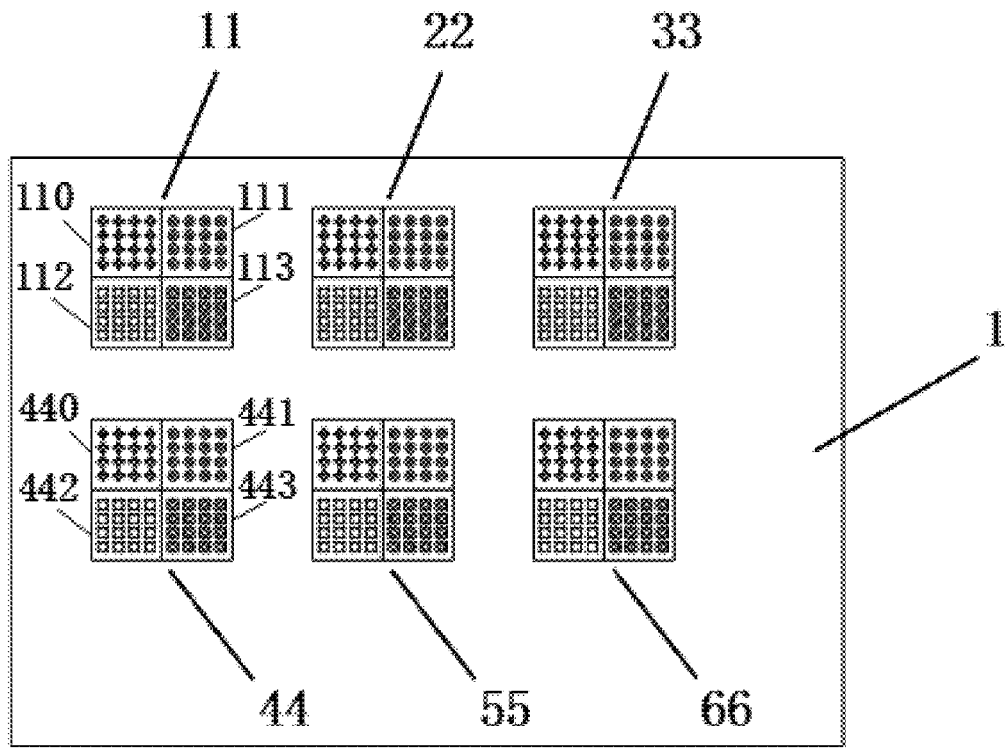
FIG. 7 is a top view of yet another optical filter layer according to an exemplary embodiment of the present application.
Figure 8:
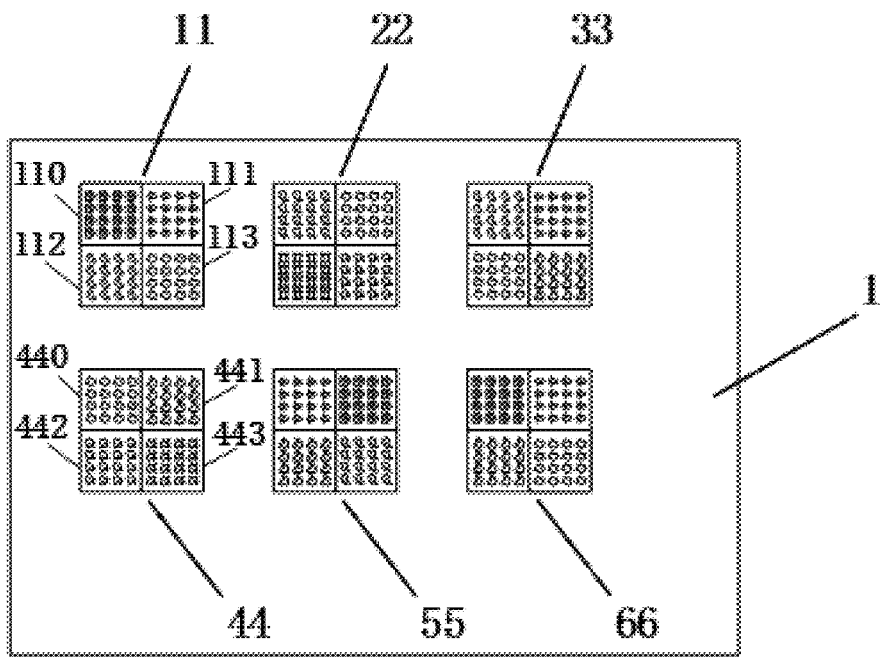
FIG. 8 is a top view of still another optical filter layer according to an exemplary embodiment of the present application.
Figure 9:
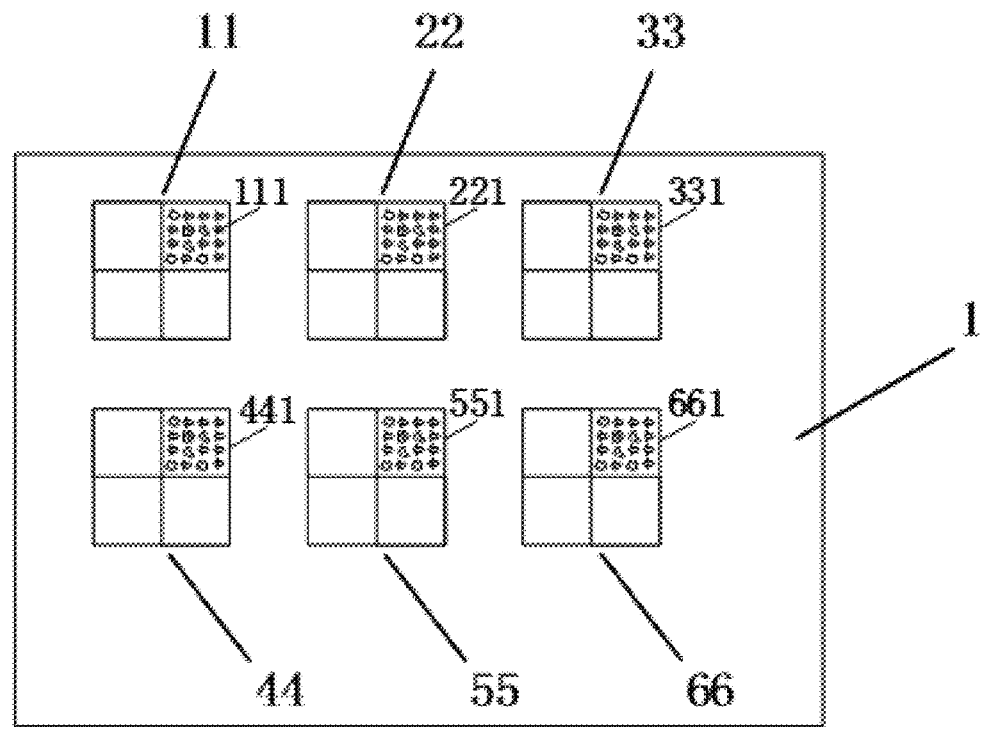
FIG. 9 is a top view of yet another optical filter layer according to an exemplary embodiment of the present application.

Hereinafter, an example will be described with reference to FIGS. 5 to 9. In this embodiment, as shown in FIG. 5, the optical filter layer 1 includes a plurality of repeated continuous or discrete micro-nano units, such as 11, 22, 33, 44, 55, 66. Each micro-nano unit has the same structure that is an aperiodic structure, and each micro-nano unit corresponds to one or more pixels on the image sensor 2. As shown in FIG. 6, the optical filter layer 1 includes a plurality of repeated micro-nano units, such as 11, 22, 33, 44, 55, 66. Each micro-nano unit has the same structure (the difference from FIG. 5 is that each micro-nano unit in FIG. 6 has a periodic structure), each micro-nano unit corresponds to one or more pixels on the image sensor 2. As shown in FIG. 7, the optical filter layer 1 includes a plurality of repeated micro-nano units, such as 11, 22, 33, 44, 55 66. Each micro-nano unit has the same structure that is a periodic structure, and each micro-nano unit corresponds to one or more pixels on the image sensor 2. The difference from FIG. 6 is that the unit shape of the periodic array in each micro-nano unit in FIG. 7 has four-fold rotation symmetry. As shown in FIG. 8, the optical filter layer 1 includes a plurality of micro-nano units, such as 11, 22, 33, 44, 55, 66, and the difference from FIG. 6 is that each micro-nano unit has different structure from each other, and each micro-nano unit corresponds to one or more pixels on the image sensor 2. In this embodiment, the optical filter layer 1 includes a plurality of different micro-nano units. That is, different areas on the intelligent chip have different modulating effects on the incident light, thereby increasing the degree of freedom of design and further improving the accuracy of recognition. As shown in FIG. 9, the optical filter layer 1 includes a plurality of repeated micro-nano units, such as 11, 22, 33, 44, 55, and 66. Each micro-nano unit has the same structure. The difference from FIG. 5 is that each micro-nano unit is composed of a discrete aperiodic array structure, and each micro-nano unit corresponds to one or more pixels on the image sensor 2.

In this embodiment, the micro-nano unit has different modulation effects on light of different wavelengths, and specific modulation methods include, but are not limited to, scattering, absorption, interference, surface plasmons, resonance enhancement, and the like. By designing different filter structures, the corresponding transmission spectra are different after light passes through different groups of filter structures.

Based on the content of the foregoing embodiments, in an embodiment, the micro-nano unit includes a regular structure and/or an irregular structure; and/or the micro-nano unit includes a discrete structure and/or a continuous structure.

In this embodiment, the micro-nano unit may include only a regular structure, or only an irregular structure, or may include both a regular structure and an irregular structure.

In this embodiment, the micro-nano unit including a regular structure here may mean that the smallest modulation units included in the micro-nano unit have a regular structure, for example, the smallest modulation units may have regular shapes such as rectangles, squares, and circles. In addition, the micro-nano unit including a regular structure here may also mean that the smallest modulation units included in the micro-nano unit are regularly arranged, for example, arranged in a regular array form, a circular form, a trapezoidal form, a polygonal form, etc. In addition, the micro-nano unit including a regular structure may also mean that the smallest modulation units included in the micro-nano unit have a regular structure, at the same time the smallest modulation units are regularly arranged.

In this embodiment, the micro-nano unit including an irregular structure may mean that the smallest modulation units included in the micro-nano unit have an irregular structure, for example, the smallest modulation units may have regular shapes such as irregular polygons, random shapes, etc. In addition, the micro-nano unit including an irregular structure here may also mean that the smallest modulation units included in the micro-nano unit are irregularly arranged, for example, arranged in an irregular polygonal form, a random arrangement form, etc. In addition, the micro-nano unit including an irregular structure may also mean that the smallest modulation units included in the micro-nano unit have an irregular structure, at the same time the smallest modulation units are irregularly arranged.

In this embodiment, the micro-nano unit in the optical filter layer may include a discrete structure, may also include a continuous structure, or may include both a discrete structure and a continuous structure.

In this embodiment, the micro-nano unit including a continuous structure may mean that the micro-nano unit is composed of continuous modulation patterns; the micro-nano unit including a discrete structure herein may mean that the micro-nano unit is composed of discrete modulation patterns.

It may be understood that the continuous modulation pattern herein may refer to a linear pattern, a wavy line pattern, a zigzag line pattern, and so on.

It may be understood that the discrete modulation pattern here may refer to a modulation pattern formed by discrete shapes (such as discrete points, discrete triangles, discrete stars).

In this embodiment, it should be noted that different micro-nano units have different modulation effects on light of different wavelengths, and specific modulation methods include, but are not limited to, scattering, absorption, interference, surface plasmons, resonance enhancement, and the like. By designing different micro-nano units, the corresponding transmission spectra are different after light passes through different groups of micro-nano units.

Based on the content of the foregoing embodiments, in an embodiment, the micro-nano unit includes a plurality of groups of micro-nano structure arrays, and each group of the micro-nano structure arrays has the same or different structure.

Figure 10:
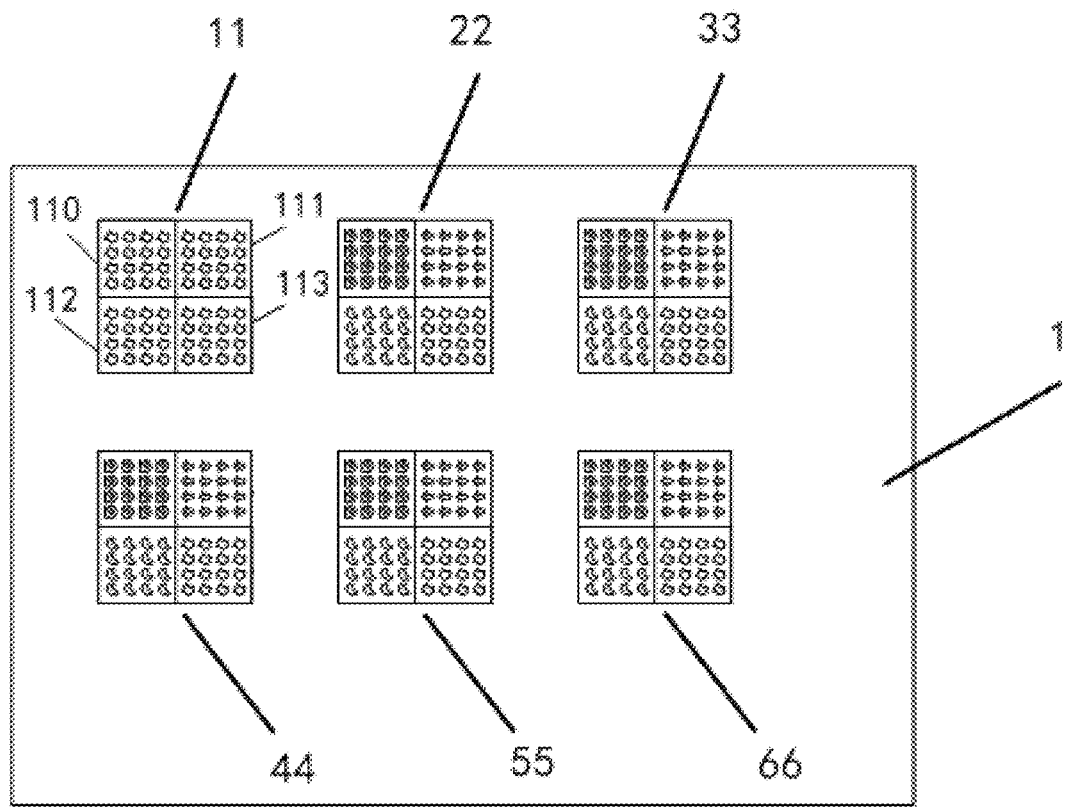
FIG. 10 is a top view of yet another optical filter layer according to an exemplary embodiment of the present application.

In this embodiment, as shown in FIG. 5, the optical filter layer 1 includes a plurality of repeated micro-nano units, such as 11, 22, 33, 44, 55, 66. Each micro-nano unit includes a plurality of groups of micro-nano structure arrays. For example, the micro-nano unit 11 includes four different periodic micro-nano structure arrays 110, 111, 112, and 113, and the micro-nano unit 44 includes four different periodic micro-nano structure arrays 440, 441, 442, and 443. As shown in FIG. 10, the optical filter layer 1 includes a plurality of repeated micro-nano units, such as 11, 22, 33, 44, 55, 66. Each micro-nano unit includes a plurality of groups of micro-nano structure arrays. For example, the micro-nano unit 11 includes four same periodic micro-nano structure arrays 110, 111, 112, and 113.

It should be noted that the micro-nano unit including four groups of micro-nano structure arrays is only used as an example for illustration, and does not play a limiting role. In practical applications, the micro-nano unit including six groups, eight groups or other numeral groups of micro-nano structure arrays may also be set as needed.

In this embodiment, each group of micro-nano structure array inside the micro-nano unit has different modulation effects on light of different wavelengths, and the modulation effects on the input light are also different between the groups of filter structures. Specific modulation methods include, but are not limited to, scattering, absorption, interference, surface plasmons, resonance enhancement, and the like. By designing different micro-nano structure arrays, the corresponding transmission spectra are different after light passes through different groups of micro-nano structure arrays.

Based on the content of the foregoing embodiments, in an embodiment, each group of micro-nano structure arrays has broadband filtering or narrow-band filtering functions.

Figure 11:
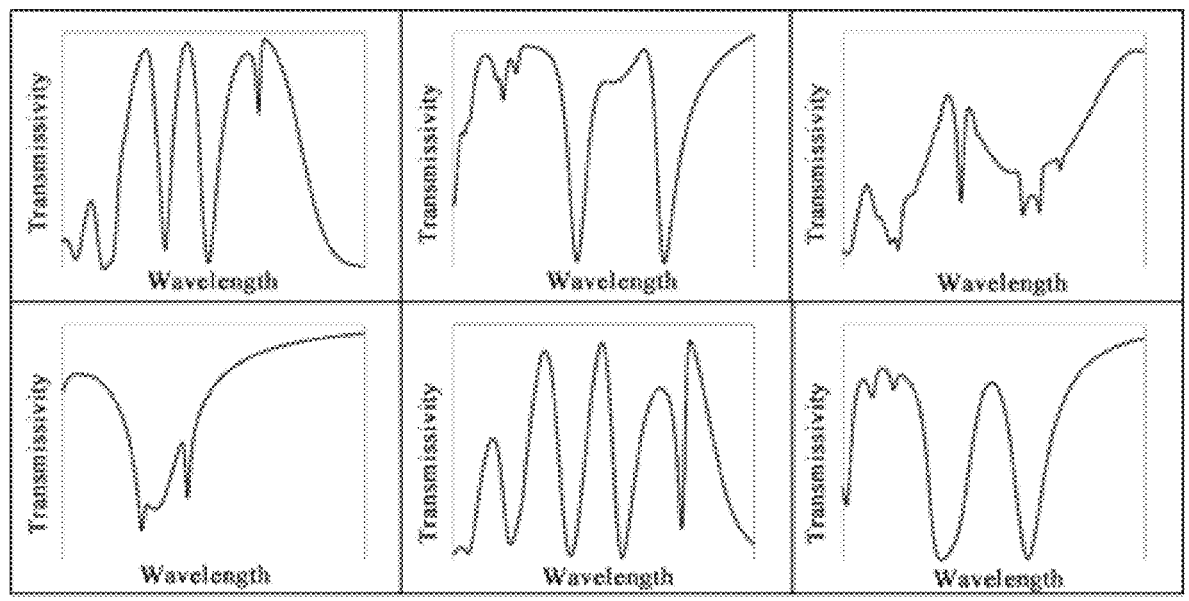
FIG. 11 is a schematic diagram showing a broadband filtering effect of a micro-nano structure according to an exemplary embodiment of the present application.
Figure 12:
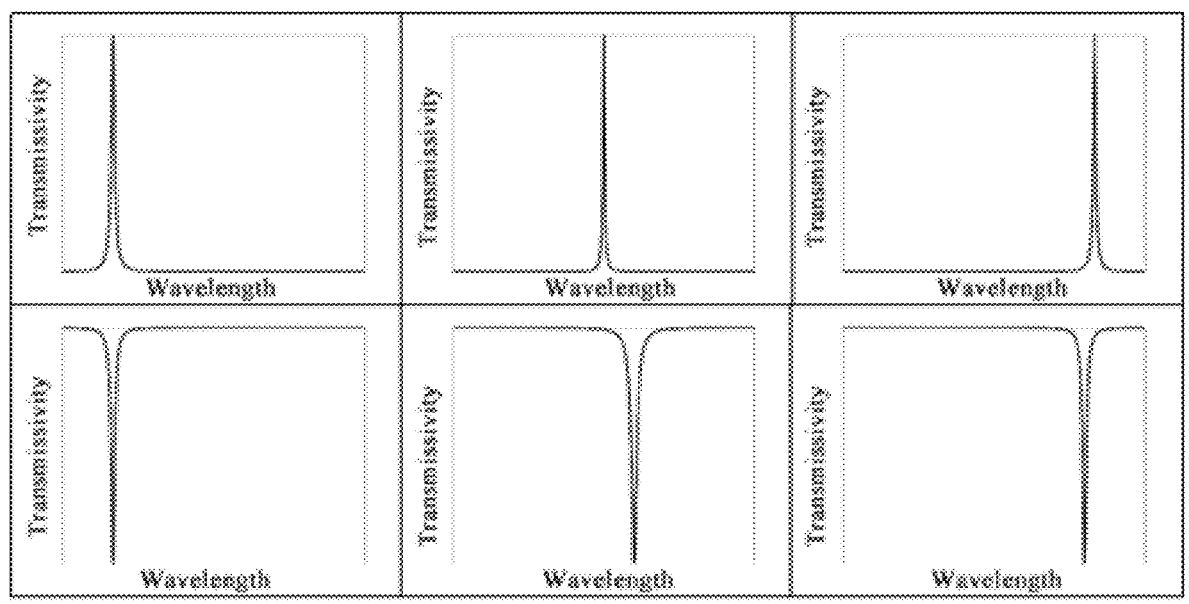
FIG. 12 is a schematic diagram showing a narrowband filtering effect of a micro-nano structure according to an exemplary embodiment of the present application.

In this embodiment, in order to obtain the modulation intensity of the different wavelength components of the incident light of the target object as the connection weight from the input layer to the linear layer of the neural network, broadband filtering and narrowband filtering are realized by using different micro-nano structure arrays. Therefore, in this embodiment, the micro-nano structure array obtains the modulation intensity of different wavelength components of the incident light of the target object by performing broadband filtering or narrowband filtering on the incident light of the target object. As shown in FIGS. 11 and 12, each group of micro-nano structure arrays in the optical filter layer has broadband filtering or narrowband filtering functions.

It may be understood that, for each group of micro-nano structure arrays, they may all have a broadband filtering function, or all may have a narrowband filtering function, or some may have a broadband filtering function while some may have a narrowband filtering function. In addition, each group of micro-nano structure arrays may also have the same or different broadband filtering ranges and narrowband filtering ranges. For example, by designing the period, duty cycle, radius, side length and other size parameters of each group of micro-nano structure in the micro-nano unit, it has a narrowband filtering effect, that is, only allowing one (or fewer) wavelengths of light to pass. For another example, by designing the period, duty cycle, radius, side length and other size parameters of each group of micro-nano structures in the micro-nano unit, it has a broadband filtering effect, that is, allowing more or all wavelengths of light to pass.

It can be understood that, in specific use, the filtering state of each group of micro-nano structure arrays may be determined by performing broadband filtering, narrowband filtering, or a combination thereof according to the application scenario.

Based on the content of the foregoing embodiments, in an embodiment, each group of micro-nano structure arrays is a periodic structure array or an aperiodic structure array.

In this embodiment, each group of micro-nano structure arrays may all be periodic structure arrays, all may be aperiodic structure arrays, or part thereof are periodic structure arrays while a part thereof are aperiodic structure arrays. The periodic structure array is easy to perform optical simulation design, and the periodic structure array may provide more complex modulation effects.

In this embodiment, as shown in FIG. 5, the optical filter layer 1 includes a plurality of repeated micro-nano units, such as 11, 22, 33, 44, 55, 66. Each micro-nano unit is composed of a plurality of groups of micro-nano structures. Each micro-nano structure array has different structures from each other, and the micro-nano structure array is an aperiodic structure. The periodic structure refers to the shapes of the modulation holes on the micro-nano structure array are arranged in an aperiodic manner. As shown in FIG. 5, the micro-nano unit 11 includes four different periodic micro-nano structure arrays 110, 111, 112, and 113, and the micro-nano unit 44 includes four different periodic micro-nano structure arrays 440, 441, 442, and 443. The micro-nano structure array of aperiodic structure is obtained by designing and training neural network data for intelligent processing tasks in the early stage, and it is usually an irregular-shaped structure. As shown in FIG. 5, the optical filter layer 1 includes a plurality of repeated micro-nano units, such as 11, 22, 33, 44, 55, 66. Each micro-nano unit is composed of a plurality of groups of micro-nano structures. Each micro-nano structure array has different structures from each other, and the difference from FIG. 5 is that the micro-nano structure array is a periodic structure. The periodic structure refers to the shapes of the modulation holes on the micro-nano structure array are arranged in an aperiodic manner and the size of the period is usually 20 nm to 50 µm. As shown in FIG. 6, the micro-nano unit 11 includes four different periodic micro-nano structure arrays 110, 111, 112, and 113, and the micro-nano unit 44 includes four different periodic micro-nano structure arrays 440, 441, 442, and 443. The filter structure of periodic structure is obtained by designing and training neural network data for intelligent processing tasks in the early stage, and it is usually an irregular-shaped structure. As shown in FIG. 7, the optical filter layer 1 includes a plurality of micro-nano units, such as 11, 22, 33, 44, 55, 66 different from each other. Each micro-nano unit is composed of a plurality of groups of micro-nano structures. Each micro-nano structure array has different structures from each other, and the micro-nano structure array is a periodic structure. The periodic structure refers to the shapes of the modulation holes on the filter structure are arranged in an aperiodic manner and the size of the period is usually 20 nm to 50 μm. As shown in FIG. 7, the micro-nano structure arrays of the micro-nano unit 11 and the micro-nano unit 12 are different from each other. The micro-nano unit 11 includes four different periodic micro-nano structure arrays 110, 111, 112, and 113, and the micro-nano unit 44 includes four different periodic micro-nano structure arrays 440, 441, 442, and 443. The micro-nano structure array of periodic structure is obtained by designing and training neural network data for intelligent processing tasks in the early stage, and it is usually an irregular-shaped structure.

It should be noted that each micro-nano unit in FIGS. 5 to 9 includes four groups of micro-nano structure arrays. The four groups of micro-nano structure arrays are respectively formed by four different shapes of modulation holes. The four groups of micro-nano structure arrays are configured to have different modulation effects on the incident light. It should be noted that the micro-nano unit including four groups of micro-nano structure arrays is only used as an example for illustration, and does not play a limiting role. In practical applications, the micro-nano unit including six groups, eight groups or other numeral groups of micro-nano structure arrays may also be set as needed. In this embodiment, the four different shapes may be a circle, a cross, a regular polygon, and a rectangle (not limited to this).

In this embodiment, each group of micro-nano structure array inside the micro-nano unit has different modulation effects on light of different wavelengths, and the modulation effects on the input light are also different between the each group of micro-nano structure arrays. Specific modulation methods include, but are not limited to, scattering, absorption, interference, surface plasmons, resonance enhancement, and the like. By designing different micro-nano structure arrays, the corresponding transmission spectra are different after light passes through different groups of micro-nano structure arrays.

Based on the content of the foregoing embodiments, in an embodiment, one or more groups of empty structures are present in the plurality of groups of micro-nano structure arrays contained in the micro-nano unit.

An embodiment is given below with reference to the example shown in FIG. 9. in this embodiment, as shown in FIG. 9, the optical filter layer 1 includes a plurality of repeated micro-nano units, such as 11, 22, 33, 44, 55, 66. Each micro-nano unit is composed of a plurality of groups of micro-nano structure arrays. The corresponding structures of the plurality of groups of micro-nano structure arrays are different from each other. The micro-nano structure arrays are periodic structures. The difference from the above-mentioned embodiment is that any micro-nano unit includes one or more groups of empty structures, which are configured to allow incident light to pass directly. It may be understood that when the plurality of groups of micro-nano structure arrays include one or more groups of empty structures, a richer spectrum modulation effect may be formed, so as to meet the spectrum modulation requirements under specific scenarios, or meet the specific connection weight requirement between the input layer and the linear layer under specific scenarios.

As shown in FIG. 9, each micro-nano unit includes a group of micro-nano structure arrays and three groups of empty structures. The micro-nano unit 11 includes a periodic micro-nano structure array 111, and the micro-nano unit 22 includes an aperiodic structure array 221. The micro-nano unit 33 includes an aperiodic structure array 331, the micro-nano unit 44 includes a periodic micro-nano structure array 441, the micro-nano unit 55 includes an aperiodic micro-nano structure array 551, and the micro-nano unit 66 includes an aperiodic structure micro-nano array 661, in which the micro-nano structure array is configured to modulate the incident light differently. It should be noted that the micro-nano unit including a group of micro-nano structure arrays and three groups of empty structures is only used as an example for illustration, and does not play a limiting role. In practical applications, the micro-nano unit including a group of micro-nano structure arrays and five groups of empty structures may also be set as needed. In this embodiment, the micro-nano structure array may be made with circular, cross, regular polygon and rectangular modulation holes (not limited to this).

It should be noted that the plurality of groups of micro-nano structure arrays contained in the micro-nano unit may include no empty structures, that is, the plurality of groups of micro-nano structure arrays may be aperiodic structure arrays or periodic structure arrays.

Based on the content of the foregoing embodiments, in an embodiment, the micro-nano unit has polarization-independent characteristics.

In this embodiment, since the micro-nano unit has polarization-independent characteristics, the optical filter layer is made insensitive to the polarization of incident light, thereby implementing an optical artificial neural network intelligent chip that is insensitive to incident angle and polarization. The optical artificial neural network intelligent chip according to the embodiment of the present application is insensitive to the incident angle and polarization characteristics of incident light, that is, the measurement result will not be affected by the incident angle and polarization characteristics of the incident light, thereby ensuring the stability of the spectral measurement performance and further ensuring the stability of intelligent processing, such as the stability of intelligent perception, the stability of intelligent recognition, the stability of intelligent decision-making, and so on. It should be noted that the micro-nano unit may also have polarization-dependent characteristics.

Based on the content of the foregoing embodiments, in an embodiment, the micro-nano unit has four-fold rotation symmetry.

In this embodiment, it should be noted that the four-fold rotation symmetry is a specific case of polarization-independent characteristics. By designing the micro-nano unit as a structure with four-fold rotation symmetry, the requirements for polarization-independent characteristics may be met.

An embodiment is given below with reference to the example shown in FIG. 7. in this embodiment, as shown in FIG. 7, the optical filter layer 1 includes a plurality of repeated micro-nano units, such as 11, 22, 33, 44, 55, 66. Each micro-nano unit is composed of a plurality of groups of micro-nano structure arrays. The corresponding structures of the plurality of groups of micro-nano structure arrays are different from each other. The micro-nano structure arrays are periodic structures. The difference from the above-mentioned embodiment is that the corresponding structure of each group of micro-nano structure array may be a circle, cross, regular polygon, rectangle and other structures with four-fold rotation symmetry, that is, after the structure is rotated by 90°, 180°, 270°, it overlaps with the original structure, so that the structure has polarization-independent characteristics, and the same intelligent recognition effect may be provided in different polarized light incidents.

Based on the content of the foregoing embodiments, in an embodiment, the optical filter layer is composed of one or more filter layers;
the filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

The semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nano-pillar two-dimensional materials, and nanowire two-dimensional materials.

Photonic crystals, as well as a combination of metasurfaces and random structures may be compatible with CMOS technology and have a better modulation effect. The micro-nano modulation structure may also be filled with other materials to smooth the surface. Quantum dots and perovskite may use the spectral modulation characteristics of the material itself to minimize the volume of a single modulation structure. SPP is small in size and may provide polarization-related optical modulation. Liquid crystal may be dynamically adjusted with voltage to improve spatial resolution. The tunable Fabry-Perot resonant cavity may be dynamically adjusted to improve the spatial resolution.

Based on the content of the foregoing embodiments, in an embodiment, the optical filter layer has a thickness of $0.1\lambda$-$10\lambda$, where $\lambda$ represents the center wavelength of incident light.

In this embodiment, it should be noted that if the optical filter layer has the thickness of much smaller than the central wavelength of the incident light, it cannot provide an effective spectrum modulation effect; if the optical filter layer has the thickness of much larger than the central wavelength of the incident light, it is difficult to prepare in term of a process and greater optical loss will be produced. Therefore, in this embodiment, in order to reduce the optical loss and facilitate preparation, and to ensure effective spectrum modulation, the overall size (area) of each micro-nano unit in the optical filter layer 1 is usually $\lambda^2$ to $10^5\lambda^2$, and the thickness is usually $0.1\lambda$~$10\lambda$, ($\lambda$ represents the center wavelength of the incident light of the target object). As shown in FIG. 5, the overall size of each micro-nano unit is 0.5 $\mu m^2$ to 40000 $\mu m^2$, the dielectric material in the optical filter layer 1 is polysilicon, and the thickness is 50 nm to 2 $\mu m$.

Based on the content of the foregoing embodiments, in an embodiment, the image sensor is any one or more of the following:
CMOS image sensor (CIS), Charge Coupled Device (CCD), Single Photon Avalanche Diode (SPAD) array and focal plane photodetector array.

In this embodiment, it should be noted that using wafer-level CMOS image sensor CIS, monolithic integration at the wafer level is implemented, and the distance between the image sensor and the optical filter layer may be minimized, which is beneficial for decreasing the size of the unit and reducing the device volume and packaging cost. SPAD may be used for weak light detection and CCD may be used for strong light detection.

In this embodiment, the optical filter layer and the image sensor may be manufactured by a complementary metal oxide semiconductor (CMOS) integrated process, which is beneficial to decrease the failure rate of the device, increase the yield of the device, and reduce the cost. For example, the optical filter layer may be prepared by directly growing one or more layers of dielectric materials on the image sensor, and then etching, depositing a metal material before removing a sacrificial layer for etching, and finally removing the sacrificial layer.

Based on the content of the foregoing embodiments, in an embodiment, the artificial neural network includes a feed-forward neural network.

In this embodiment, the feedforward neural network (FNN), also known as a deep feedforward network (DFN) and multi-layer perceptron (MLP), is one of the simplest neural networks in which each neuron is arranged in layers. Each neuron is only connected to the neuron of the previous layer. The output of the previous layer is received and outputted to the next layer without feedback between the layers. The feedforward neural network has a simple structure, is easy to implement on hardware, and has a wide range of applications. It can approximate any continuous function and square integral function with arbitrary precision. Also, any limited training sample set may be accurately realized. The feedforward neural network is a static nonlinear mapping. Through the composite mapping of simple nonlinear processing units, complex nonlinear processing capabilities may be obtained.

Based on the content of the foregoing embodiments, in an embodiment, a light-permeable medium layer is provided between the optical filter layer and the image sensor.

In this embodiment, it should be noted that the provision of a light-permeable medium layer between the optical filter layer and the image sensor may effectively separate the optical filter layer from the image sensor layer and avoid mutual interference therebetween.

Based on the content of the foregoing embodiments, in an embodiment, the image sensor is a front-side illuminated type, and includes a metal wire layer and a light detection layer arranged from top to bottom, and the optical filter layer is integrated on a side of the metal wire layer away from the light detection layer.

Alternatively, the image sensor is a back-side illuminated type, and includes a light detection layer and a metal wire layer arranged from top to bottom, and the optical filter layer is integrated on a side of the light detection layer away from the metal wire layer.

Figure 13:
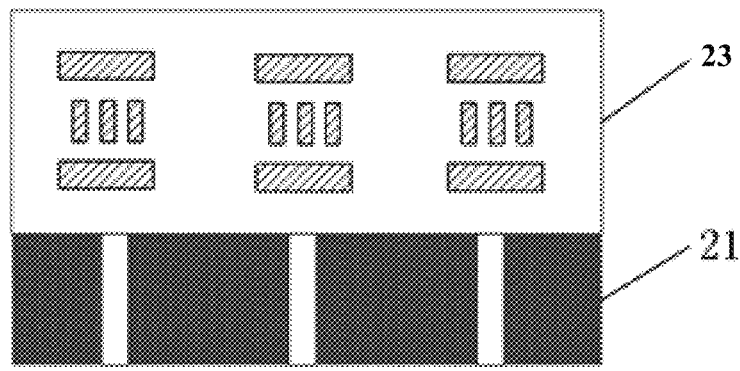
FIG. 13 is a schematic structural diagram of a front-side illuminated image sensor according to an exemplary embodiment of the present application.

In this embodiment, FIG. 13 shows a front-side illuminated image sensor in which a silicon detection layer 21 is under a metal wire layer 23, and the optical filter layer 1 is directly integrated on the metal wire layer 23.

Figure 14:
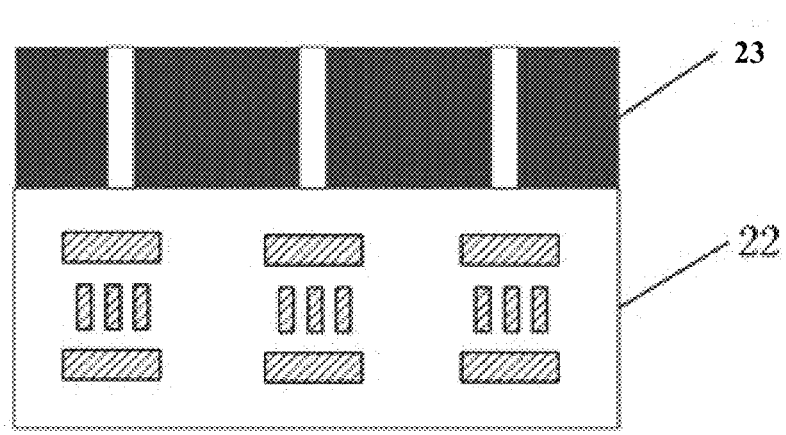
FIG. 14 is a schematic structural diagram of a back-side illuminated image sensor according to an exemplary embodiment of the present application.

In this embodiment, unlike FIG. 13, FIG. 14 shows a back-side illuminated image sensor in which a silicon detection layer 21 is above a metal wire layer 23, and the optical filter layer 1 is directly integrated on the silicon detection layer 21.

It should be noted that for a back-side illuminated image sensor, the silicon detection layer 21 is above the metal wire layer 23, which may reduce the influence of the metal wire layer on incident light, thereby improving the quantum efficiency of the device.

According to the above content, in this embodiment, the optical filter layer serves as the input layer of the artificial neural network, the image sensor serves as the linear layer of the artificial neural network, and the filtering effect of the optical filter layer on the incident light entering the optical filter layer serves as the connection weight from the input layer to the linear layer. The optical filter layer and the image sensor in the optical artificial neural network intelligent chip provided in this embodiment realizes the related functions of the input layer and the linear layer in the artificial neural network through hardware, so that no complicated signal processing and algorithm processing corresponding to the input layer and the linear layer need to be performed in the subsequent artificial neural network intelligent processing using the intelligent chip, which may greatly reduce the power consumption and delay of artificial neural network processing. In addition, in this embodiment, since the image information of the target object and spectral information at different points in the space are simultaneously utilized in this embodiment, the intelligent processing of the target object may be realized more accurately.

Based on the same inventive concept, another embodiment of the present application provides an intelligent processing apparatus, including the optical artificial neural network intelligent chip as described in the above embodiments. The intelligent processing apparatus includes one or more of a smart phone, a smart computer, an intelligent identification device, an intelligent perception device, and an intelligent decision device.

Since the intelligent processing apparatus according to this embodiment includes the optical artificial neural network intelligent chip described in the foregoing embodiments, the intelligent processing apparatus according to this embodiment has all the beneficial effects of the optical artificial neural network intelligent chip described in the foregoing embodiments. Since this has been described in more detail in the foregoing embodiments, it will not be repeated in this embodiment.

Figure 15:
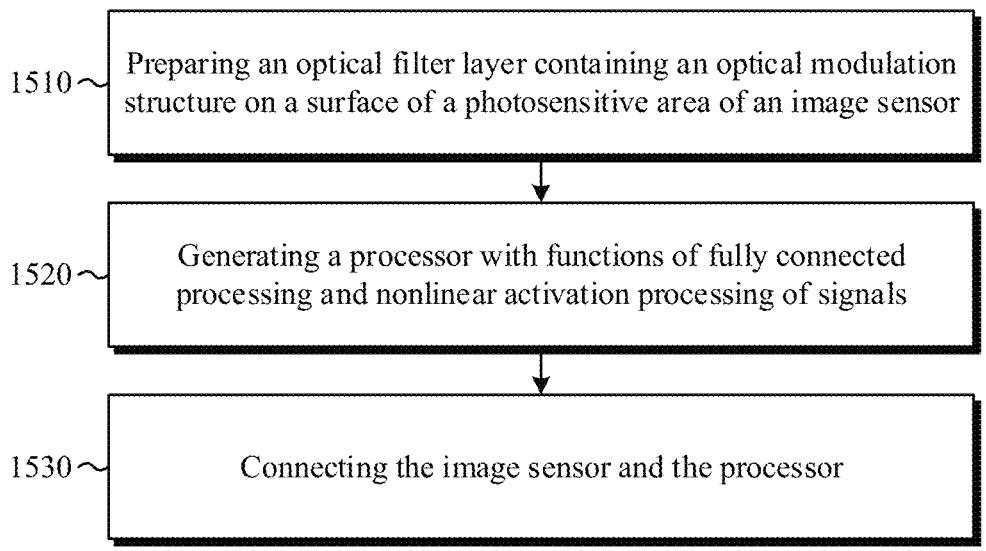
FIG. 15 is a schematic flowchart of a method for preparing an optical artificial neural network intelligent chip according to the third exemplary embodiment of the present application.

Based on the same inventive concept, another embodiment of the present application provides a method for preparing an optical artificial neural network intelligent chip as described in the above-mentioned embodiments, as shown in FIG. 15, it specifically includes the following steps:
  step 1510: preparing an optical filter layer containing an optical modulation structure on a surface of a photosensitive area of an image sensor;
  step 1520: generating a processor with the functions of fully connected processing and nonlinear activation processing of signals; and
  step 1530: connecting the image sensor and the processor;
  wherein the optical filter layer is configured to modulate, with different spectra incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and
  the image sensor is configured to convert information carried in the incident light corresponding to different location points after being modulated by the optical filter layer into electric signals corresponding to the different location points, and send the electric signals corresponding to the different location points to the processor; and the processor is configured to perform fully connected processing and nonlinear activation processing on the electrical signals corresponding to the different location points to obtain output signals of the artificial neural network.

The preparing an optical filter layer containing an optical modulation structure on a surface of a photosensitive area of an image sensor includes:
  growing one or more layers of preset materials on the surface of the photosensitive area of the image sensor;
  dry etching a pattern of the optical modulation structure on the one or more layers of preset materials to obtain the optical filter layer containing the optical modulation structure; or
  performing imprint transfer on the one or more layers of preset materials to obtain the optical filter layer containing the optical modulation structure; or
  performing additional dynamic modulation on the one or more layers of preset materials to obtain the optical filter layer containing the optical modulation structure; or
  performing zonal printing on the one or more layers of preset materials to obtain the optical filter layer containing the optical modulation structure; or
  performing zonal growth on the one or more layers of preset materials to obtain the optical filter layer containing the optical modulation structure; or
  performing quantum dot transfer on the one or more layers of preset materials to obtain the optical filter layer containing the optical modulation structure.

When the optical artificial neural network intelligent chip is used for the intelligent processing task of the target object, an optical modulation structure, an image sensor and an processor satisfying the training convergence condition are obtained by training the optical artificial neural network intelligent chip containing different optical modulation structures, image sensors, and processors with different fully connected parameters and nonlinear activation parameters using input training samples and output training samples corresponding to the intelligent processing task.

In this embodiment, it should be noted that, as shown in FIG. 1, the optical filter layer 1 may be prepared by directly growing one or more layers of dielectric materials on the image sensor 2, and then etching, depositing a metal material before removing a sacrificial layer for etching, and finally removing the sacrificial layer. By designing the size parameters of the optical modulation structure, each unit may have different modulation effects on the light of different wavelengths in the target range, and the modulation effect is insensitive to the incident angle and polarization. Each unit in the optical filter layer 1 corresponds to one or more pixels on the image sensor 2. The optical filter layer 1 is prepared directly on the image sensor 2.

In this embodiment, it should be noted that, as shown in FIG. 14, assuming that the image sensor 2 has a back-side illuminated structure, the optical filter layer 1 may be prepared by directly etching on the silicon detection layer 21 of the back-side illuminated image sensor and then depositing metal.

In addition, it should be noted that the optical modulation structure on the optical filter layer may be prepared by dry etching optical modulation structure patterns on one or more layers of preset materials, wherein the dry etching refers to directly removing unnecessary parts of one or more layers of preset materials on the surface of the photosensitive area of the image sensor to obtain the optical filter layer containing the optical modulation structure; or by performing imprint transfer on the one or more layers of preset materials to obtain the optical filter layer containing the optical modulation structure, wherein the imprint transfer refers to preparing a required structure by etching on other substrate and transferring the required structure to the photosensitive area of the image sensor through materials such as PDMS; or by performing additional dynamic modulation on the one or more layers of preset materials to obtain the optical filter layer containing the optical modulation structure, wherein the additional dynamic modulation refers to using active materials, and then adding electrodes to control the optical modulation characteristics of the corresponding area by changing the voltage; or by performing zonal printing on the one or more layers of preset materials to obtain the optical filter layer containing the optical modulation structure, wherein the zonal printing refers to a technique of printing in a zonal manner; or by performing zonal growth on the one or more layers of preset materials to obtain the optical filter layer containing the optical modulation structure; or by performing quantum dot transfer on the one or more layers of preset materials to obtain the optical filter layer containing the optical modulation structure.

In addition, it should be noted that, since the preparation method provided in this embodiment is the preparation method of the optical artificial neural network intelligent chip in the above embodiment, for details of some principles and structures, please refer to the description of the above embodiments, and this description will not be repeated in this embodiment.

It may be understood that face recognition technology is a kind of biometric recognition technology, which is widely used in fields such as access control and attendance systems, criminal investigation systems, and e-commerce. The main process of face recognition includes collection of face images, preprocessing, extraction of features, matching and recognition. However, it is difficult to ensure the accuracy of recognition using only the image information of the face. For example, it is difficult to distinguish a real face from a face photo; even if the depth information is combined, it is difficult to distinguish a face model from a real face. Therefore, it is of great significance to mine more face information to provide higher accuracy, safe and reliable fast face recognition.

To this end, based on the optical artificial neural network intelligent chip described in the previous embodiment, this embodiment provides a new optoelectronic chip for accurate face recognition. In the optoelectronic chip, the optical filter layer constitutes the input layer and the connection weight from the input layer to the linear layer of the optical artificial neural network; and the image sensors constitutes the linear layer of the optical artificial neural network. By collecting the image information and spectral information of the face to be recognized, fast, accurate, safe and reliable face recognition may be provided. This embodiment will be specifically explained and described in detail below.

An embodiment of the present application also provides an optical artificial neural network face recognition chip for face recognition processing tasks, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and the incident light includes the reflected light of the user's face;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer; and the processor is configured to perform fully connected processing and nonlinear activation processing on the electrical signals corresponding to the different location points to obtain face recognition processing results.

This embodiment provides a new optical artificial neural network face recognition chip capable of implementing artificial neural network functions, which is used for face recognition tasks. In the embodiment of the present application, the artificial neural network is embedded in the hardware chip, and the optical filter layer on the hardware chip serves as the input layer and the connection weight from the input layer to the linear layer of the artificial neural network. The image sensor on the hardware chip serves as the linear layer of the artificial neural network. The spatial spectrum information of the face is incident on the pretrained hardware chip, and the artificial neural network analysis is performed on the spatial spectrum information of the face by hardware chip to obtain the face recognition result. It should be noted that low power consumption and safe, reliable, fast and accurate face recognition is provided in the embodiment of the present application.

It may be understood that in the optical artificial neural network face recognition chip, an optical filter layer, that is a hardware structure thereon corresponds to an input layer and a connection weight from the input layer to a linear layer of an artificial neural network; the image sensor, that is a hardware structure thereon corresponds to the linear layer of the artificial neural network; and the processor corresponds to a nonlinear layer and an output layer of the artificial neural network. Specifically, the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area through the optical modulation structure. Accordingly, the image sensor is configured to convert the information carried in the incident light corresponding to different location points after being modulated by the optical filter layer into electric signals corresponding to the different location points, and at the same time, the processor connected with the image sensor is configured to perform fully connected processing and nonlinear activation processing on the electrical signals corresponding to the different location points to obtain output signals of the artificial neural network. In the face recognition chip, the optical filter layer serves as the input layer of the artificial neural network, the image sensor serves as the linear layer of the artificial neural network. At the same time, the filtering effect of the optical filter layer on the incident light entering the optical filter layer corresponds to the connection weight from the input layer to the linear layer, that is, the optical filter layer and the image sensor of the face recognition chip provide related functions of the input layer and the linear layer in the artificial neural network. That is, in the embodiment of the present application, the input layer and the linear layer in the artificial neural network implemented by software are stripped and the two-layer structure of the input layer and the linear layer in the artificial neural network is implemented by hardware, so that no complicated signal processing and algorithm processing corresponding to the input layer and the linear layer need to be performed in the subsequent artificial neural network face recognition processing using the face recognition chip and the processor in the face recognition chip only needs to perform fully connected processing and nonlinear activation processing on the electrical signals, which may greatly reduce the power consumption and delay of artificial neural network face recognition. In the embodiment of the present application, the optical filter layer serves as the input layer of the artificial neural network, the image sensor serves as the linear layer of the artificial neural network, the filtering effect of the optical filter layer on the incident light entering the optical filter layer serves as the connection weight from the input layer to the linear layer; spatial spectral information of a face is projected into electrical signals using the optical filter layer and the image sensor and the fully connected processing and nonlinear activation processing on the electrical signals are then implemented in the processor. Also, in the embodiment of the present application, the complicated signal processing and algorithm processing corresponding to the input layer and linear layer may not only be omitted and the image information of the face, spectral information, angle information of the incident light and phase information of the incident light, that is, the information carried by the incident light at different points in the face space may but also actually simultaneously utilized. Since the information carried by the incident light at different points in the face space covers information of the face such as images, composition, shape, three-dimensional depth, structure and the like, the information of the face such as images, composition, shape, three-dimensional depth, structure and the like is covered when the recognition processing is performed according to the information carried by the incident light at different points in the face space, such that face recognition may be performed accurately.

Further, the optical artificial neural network face recognition chip includes a trained optical modulation structure, an image sensor and a processor;

the trained optical modulation structure, an image sensor and a processor refer to an optical modulation structure, an image sensor and an processor satisfying the training convergence condition obtained by training the optical artificial neural network face recognition chip containing different optical modulation structures, image sensors, and processors with different fully connected parameters and different nonlinear activation parameters using input training samples and output training samples corresponding to a face recognition task; and the input training samples include incident light reflected by different faces; and the output training samples include corresponding face recognition results.

Further, when the optical artificial neural network face recognition chip containing different optical modulation structures, image sensors, and processors with different fully connected parameters and nonlinear activation parameters is trained, the different optical modulation structures are designed and implemented in a computer optical simulation design manner.

In this embodiment, due to the addition of light spectrum modulation, an artificial neural network photoelectric chip of which the input is an object image and its spectrum may be provided, and fast, accurate, safe and reliable live face recognition may also be provided.

In this embodiment, for face recognition, the faces of a large number of people may be collected first, and the weights from the input layer to the linear layer, that is, a system function of the optical filter layer may be obtained through data training. The required optical filter layer may be reversely designed and the designed optical filter layer is integrated above the image sensor. In actual training, the weight of the electrical signal fully connected layer is further trained and optimized using face samples to be recognized and the output of the completed optical filter layer to implement a high-accuracy optical artificial neural network and thus fast and accurate recognition of the user's face is completed.

It may be understood that the specific modulation pattern of the modulation structure on the optical filter layer is obtained by collecting the faces of a large number of people in the early stage, and is designed by artificial neural network data training. The modulation pattern usually has an irregularly shaped structure, of course, it may also have regularly shaped structure.

Figure 16:
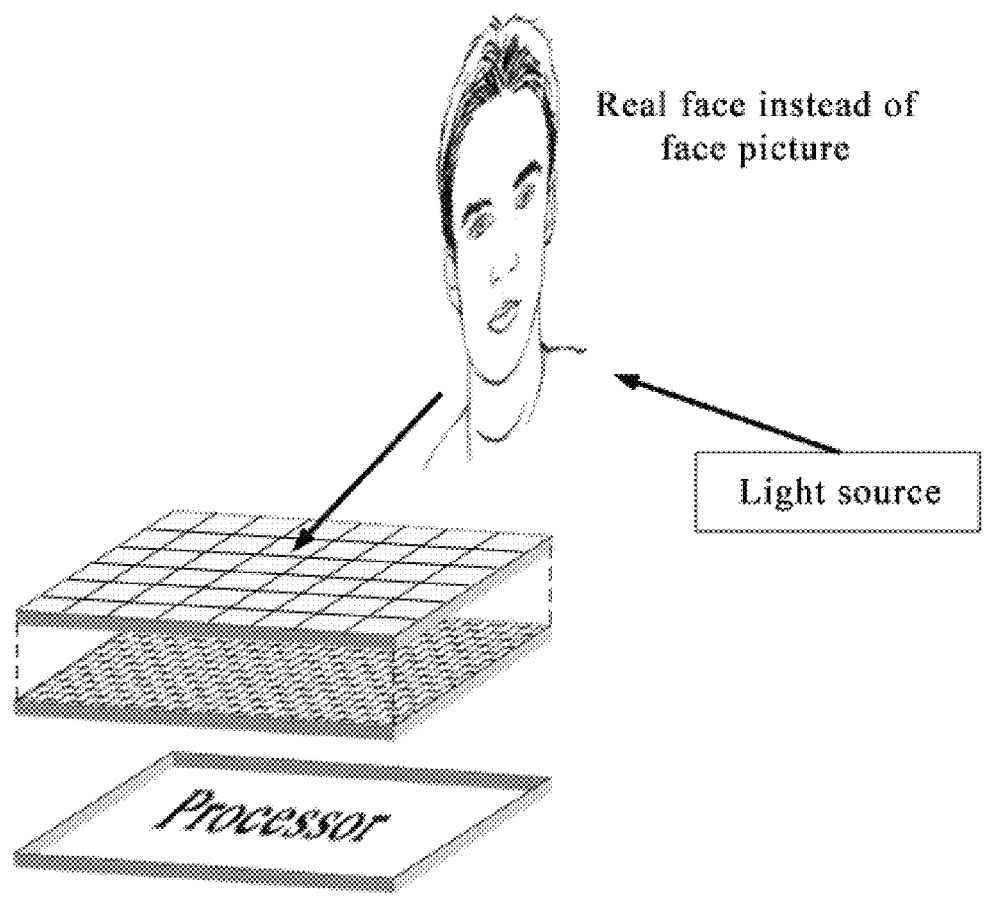
FIG. 16 is a schematic diagram of a face recognition process according to an exemplary embodiment of the present application.

As shown in FIG. 16, the complete process for face recognition includes: allowing ambient light or other light sources to irradiate the user's face, collecting the reflected light by the chip, and internally processing the reflected light to obtain the recognition result.

It may be understood that the chip actually uses the image information of the face, the spectral information, the angle information of the incident light, and the phase information of the incident light at the same time, which improves the accuracy and safety of face recognition, especially may accurately exclude face models of non-living bodies. At the same time, the chip partially implements an artificial neural network on the hardware, which improves the speed of face recognition. In addition, the solution of the chip may use the traditional CMOS process to achieve mass production, reducing the volume, power consumption and cost of the device.

Further, the optical modulation structure in the optical filter layer includes a regular structure and/or an irregular structure; and/or, the optical modulation structure in the optical filter layer includes a discrete structure and/or a continuous structure.

Further, the optical filter layer has a single-layer structure or a multi-layer structure.

Further, the optical modulation structure in the optical filter layer includes a unit array composed of a plurality of micro-nano units, and each micro-nano unit corresponds to one or more pixels on the image sensor; each micro-nano unit has the same or different structure.

Further, the micro-nano unit includes a regular structure and/or an irregular structure; and/or the micro-nano unit includes a discrete structure and/or a continuous structure.

Further, the micro-nano unit includes a plurality of groups of micro-nano structure arrays, and each group of the micro-nano structure arrays has the same or different structure.

Further, each group of micro-nano structure array has the broadband filtering or narrowband filtering functions.

Further, each group of micro-nano structure arrays is a periodic structure array or an aperiodic structure array.

Further, one or more of the plurality of groups of micro-nano structure arrays contained in the micro-nano unit has empty structures.

Further, the micro-nano unit has polarization-independent characteristics.

Further, the micro-nano unit has four-fold rotation symmetry.

Further, the optical filter layer is composed of one or more filter layers.

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

Further, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nanopillar two-dimensional materials, and nanowire two-dimensional materials.

Further, the optical filter layer has a thickness of $0.1\lambda$-$10\lambda$, where $\lambda$ represents the center wavelength of the incident light.

An embodiment of the present application also provides a face recognition apparatus, including the optical artificial neural network face recognition chip as described in above embodiments. The face recognition apparatus may be a portable face recognition apparatus or a face recognition apparatus installed in a fixed position. Since the face recognition apparatus has similar beneficial effects as the aforementioned optical artificial neural network face recognition chip, it will not be repeated here.

An embodiment of the present application also provides a method for preparing the optical artificial neural network face recognition chip as described above, including:

preparing an optical filter layer containing an optical modulation structure on a surface of a photosensitive area of an image sensor;

generating a processor with the functions of fully connected processing and nonlinear activation processing of signals; and connecting the image sensor and the processor;

wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain face recognition processing results; and the electrical signals are image signals modulated by the optical filter layer and the incident light includes the reflected light of the face.

Further, the method for preparing the optical artificial neural network face recognition chip further includes a training process of the optical artificial neural network face recognition chip and specifically includes:

training the optical artificial neural network face recognition chip containing different optical modulation structures, image sensors, and processors with different fully connected parameters and different nonlinear activation parameters using input training samples and output training samples corresponding to the face recognition task to obtain an optical modulation structure, an image sensor and an processor satisfying the training convergence condition and taking the optical modulation structure, the image sensor and the processor satisfying the training convergence condition as the trained optical modulation structure, the image sensor and the processor.

Further, when the optical artificial neural network face recognition chip containing different optical modulation structures, image sensors, and processors with different fully connected parameters and nonlinear activation parameters is trained, the different optical modulation structures are designed and implemented in a computer optical simulation design manner.

It should be noted that the optical artificial neural network face recognition chip based on the micro-nano modulation structure and the image sensor according to this embodiment has the following effects: A. the artificial neural network is partially embedded in the image sensor containing various optical filter layers to provide safe, reliable, fast and accurate face recognition. B. The preparation of the chip can be completed one time by the CMOS process, which is beneficial to decrease the failure rate of the device, improve the yield of the device, and reduce the cost. C. Implement of monolithic integration at a wafer level may minimize the distance between the sensor and the optical filter layer, which is conducive to decreasing the size of the unit, reducing the volume of the device and the packaging cost.

It should be noted that for the detailed structural description of the optical artificial neural network face recognition chip according to this embodiment, reference may be made to the description of the optical artificial neural network chip in the foregoing embodiments, and in order to avoid repetitive description, it will not be described here. In addition, for the detailed description of the preparation method of the optical artificial neural network face recognition chip, reference may also be made to the description of the preparation method of the optical artificial neural network chip in the foregoing embodiment, which will not be repeated here.

At present, noninvasive blood glucose detection methods mainly include optical and radiation methods, reverse iontophoresis analysis, electromagnetic wave method, ultrasonic method, and tissue fluid extraction method. For example, the near-infrared spectroscopy detection method mainly is to irradiate the skin with near-infrared light and reflect the blood glucose concentration from the change in the intensity of the reflected light using the relationship between the blood glucose concentration and its near-infrared spectrum absorption. This method has the advantages of rapid measurement, no chemical reagents and consumables, etc. However, due to the large individual differences of the measured objects, and the obtained signals are very weak, key technical aspects such as the selection of the measurement site, the selection of measurement conditions, and the extraction of weak chemical information from overlapping spectra need to be further resolved. It is impossible to carry inconveniently due to large size of a signal processing system. There is also the subcutaneous tissue fluid detection method, which reflects the blood glucose concentration by measuring the glucose concentration of the tissue fluid exuded under the skin. According to this principle, a watch for detecting glucose may be made, and the blood glucose concentration may be continuously monitored in real time. However, this method has poor accuracy and slow response speed, so it is difficult to replace the traditional invasive blood glucose meter. Therefore, noninvasive blood glucose detection has become an urgent need for the treatment of diabetes.

To this end, based on the optical artificial neural network intelligent chip described in the previous embodiment, this embodiment provides a new optoelectronic chip for blood glucose detection. In the optoelectronic chip, the optical filter layer constitutes the input layer and the connection weight from the input layer to the linear layer of the optical artificial neural network; and the image sensors constitutes the linear layer of the optical artificial neural network. By collecting the image information and spectral information of the part of the human body to be detected, fast, accurate, safe and reliable noninvasive blood glucose detection may be provided. The present embodiment will be specifically explained and described in detail below.

The embodiment of the present application also provides an optical artificial neural network blood glucose detection chip for blood glucose detection tasks, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; wherein the incident light includes reflected light and/or transmitted light of a part of the human body to be detected;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer; and the processor is configured to perform fully connected processing and nonlinear activation processing on the electrical signals corresponding to the different location points to obtain blood glucose detection results.

The present embodiment provides a new optical artificial neural network blood glucose detection chip capable of implementing artificial neural network functions, which is used for blood glucose detection tasks. In the embodiment of the present application, the artificial neural network is embedded in the hardware chip, and the optical filter layer on the hardware chip serves as the input layer and the connection weight from the input layer to the linear layer of the artificial neural network. The image sensor on the hardware chip serves as the linear layer of the artificial neural network. The spatial spectrum information of the part of human body to be detected is incident on the pre-trained hardware chip, and the artificial neural network analysis is performed on the spatial spectrum information of the part of human body to be detected by hardware chip to obtain the blood glucose detection result. It should be noted that low power consumption and safe, reliable, fast and accurate noninvasive blood glucose detection is provided in the embodiment of the present application.

It may be understood that in the optical artificial neural network blood glucose detection chip, an optical filter layer, that is a hardware structure thereon corresponds to an input layer and a connection weight from the input layer to a linear layer of an artificial neural network; the image sensor, that is a hardware structure thereon corresponds to the linear layer of the artificial neural network; and the processor corresponds to a nonlinear layer and an output layer of the artificial neural network. Specifically, the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area through the optical modulation structure. Accordingly, the image sensor is configured to convert the information carried in the incident light corresponding to different location points after being modulated by the optical filter layer into electric signals corresponding to the different location points, and at the same time, the processor connected with the image sensor is configured to perform fully connected processing and nonlinear activation processing on the electrical signals corresponding to the different location points to obtain output signals of the artificial neural network. In the blood glucose detection chip, the optical filter layer serves as the input layer of the artificial neural network, the image sensor serves as the linear layer of the artificial neural network. At the same time, the filtering effect of the optical filter layer on the incident light entering the optical filter layer corresponds to the connection weight from the input layer to the linear layer, that is, the optical filter layer and the image sensor of the blood glucose detection chip provide related functions of the input layer and the linear layer in the artificial neural network. That is, in the embodiment of the present application, the input layer and the linear layer in the artificial neural network implemented by software are stripped and the two-layer structure of the input layer and the linear layer in the artificial neural network is implemented by hardware, so that no complicated signal processing and algorithm processing corresponding to the input layer and the linear layer need to be performed in the subsequent artificial neural network blood glucose detection processing using the blood glucose detection chip and the processor in the blood glucose detection chip only needs to perform fully connected processing and nonlinear activation processing on the electrical signals, which may greatly reduce the power consumption and delay of artificial neural network blood glucose detection. In the embodiment of the present application, the optical filter layer serves as the input layer of the artificial neural network, the image sensor serves as the linear layer of the artificial neural network, the filtering effect of the optical filter layer on the incident light entering the optical filter layer serves as the connection weight from the input layer to the linear layer; spatial spectral information of a part of human body to be detected is projected into electrical signals using the optical filter layer and the image sensor and the fully connected processing and nonlinear activation processing on the electrical signals are then implemented in the processor. Also, in the embodiment of the present application, the complicated signal processing and algorithm processing corresponding to the input layer and linear layer may not only be omitted and the image information of the part of human body to be detected, spectral information, angle information of the incident light and phase information of the incident light, that is, the information carried by the incident light at different points in blood space in the part of human body to be detected may but also actually simultaneously utilized. Since the information carried by the incident light at different points in the blood space in the part of human body to be detected covers information of the blood in the part of human body to be detected such as images, composition, shape, three-dimensional depth, structure and the like, the information of the blood in the part of human body to be detected such as images, composition, shape, three-dimensional depth, structure and the like is covered when the recognition processing is performed according to the information carried by the incident light at different points in the blood in the part of human body to be detected, such that blood glucose detection may be performed accurately.

Further, the optical artificial neural network blood glucose detection chip includes a trained optical modulation structure, an image sensor and a processor;
the trained optical modulation structure, an image sensor and a processor refer to an optical modulation structure, an image sensor and an processor satisfying the training convergence condition obtained by training the optical artificial neural network blood glucose detection chip containing different optical modulation structures, image sensors, and processors with different fully connected parameters and different nonlinear activation parameters using input training samples and output training samples corresponding to the blood glucose detection tasks; and
the input training samples include incident light reflected and transmitted and/or irradiated by parts of the human body to be detected with different blood glucose values; the output training samples include corresponding blood glucose values.

Further, when the optical artificial neural network blood glucose detection chip containing different optical modulation structures, image sensors, and processors with different fully connected parameters and nonlinear activation parameters is trained, the different optical modulation structures are designed and implemented in a computer optical simulation design manner.

In this embodiment, due to the addition of light spectrum modulation, an artificial neural network photoelectric chip of which the input is an image and its spectrum of a part of human body to be detected may be provided, and fast, accurate, safe and reliable noninvasive blood glucose detection may also be provided.

In this embodiment, for noninvasive blood glucose detection, it is possible to first collect a large number of spectral signal data corresponding to parts of the human body with blood glucose information, simulating the response of incident light through a micro-nano modulation structure by a computer, reversely designing required micro-nano modulation structure through data training, and integrating the designed micro-nano modulation structure above the image sensor. In the process of the user's blood glucose detection, the user's blood glucose level may be quickly and accurately detected by performing algorithm regression on the electrical signals modulated by incident light of different wavelengths.

It may be understood that the specific modulation pattern of the modulation structure on the optical filter layer is obtained by collecting spectral signal data corresponding to parts of the human body with blood glucose information in the early stage, and is designed by artificial neural network data training. The modulation pattern usually has an irregularly shaped structure, of course, it may also have regularly shaped structure.

Figure 17:
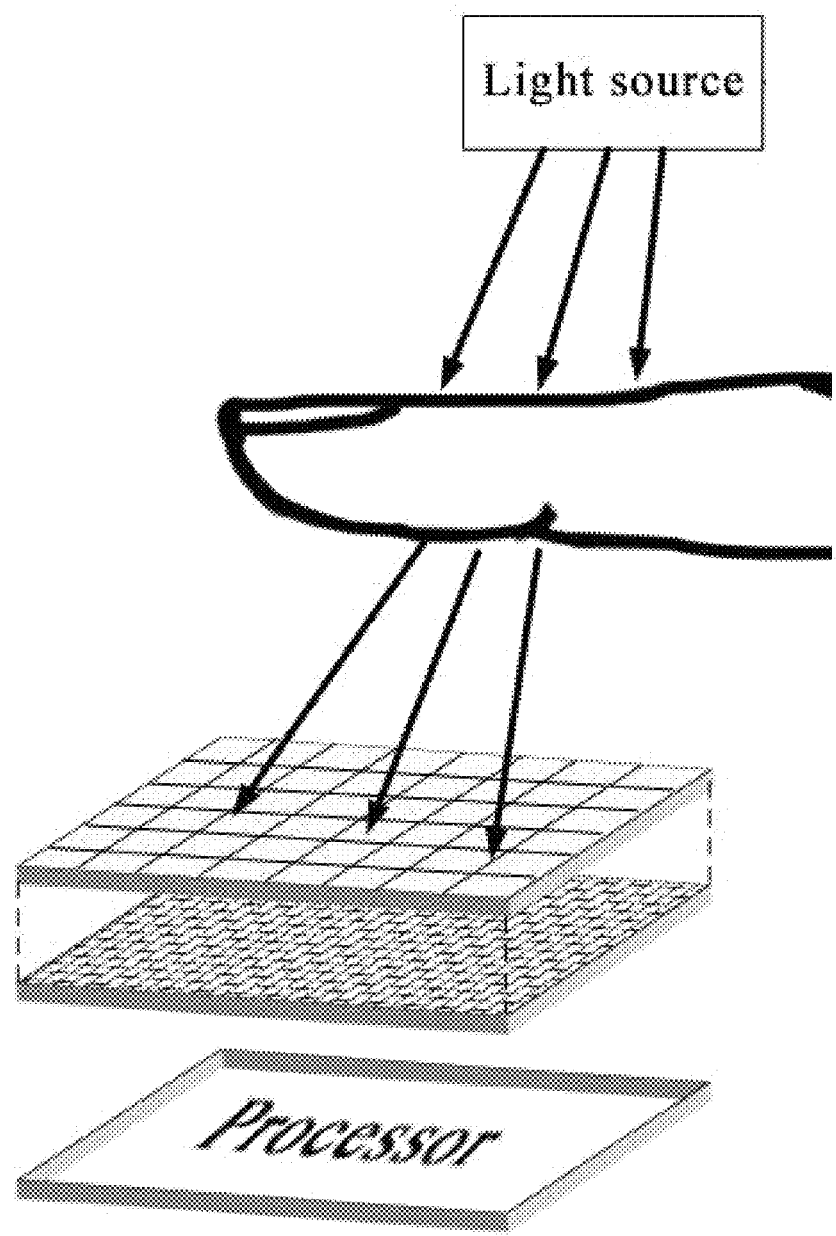
FIG. 17 is a schematic diagram of a finger blood glucose detection process according to an exemplary embodiment of the present application.
Figure 18:
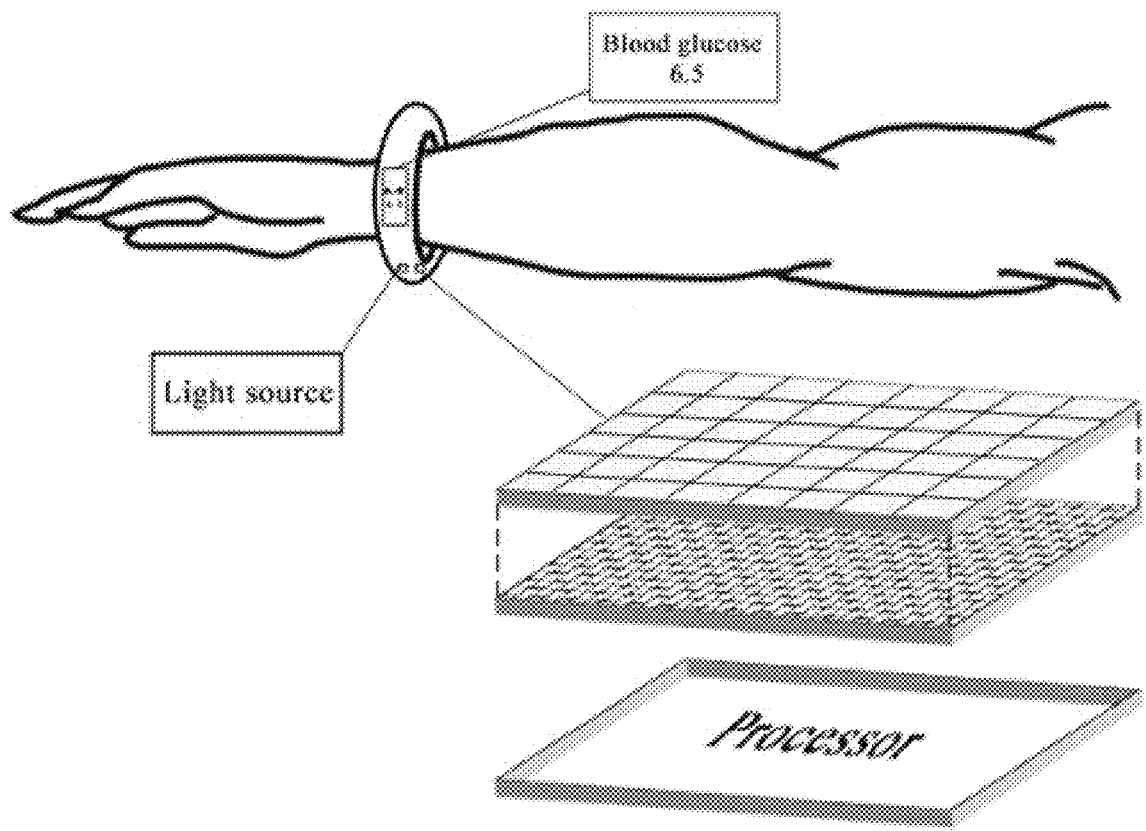
FIG. 18 is a schematic diagram of a wrist blood glucose detection process according to an exemplary embodiment of the present application.

As shown in FIG. 17, the complete process for blood glucose detection includes allowing ambient light or other light sources to irradiate a part (finger) of the human body to be detected, collecting the reflected light by the chip, and internally processing the reflected light to obtain the blood glucose detection result. As shown in FIG. 18, the complete process for blood glucose detection includes allowing ambient light or other light sources to irradiate a part (wrist) of the human body to be detected, collecting the reflected light by the chip, and internally processing the reflected light to obtain the blood glucose detection result.

It may be understood that the chip actually simultaneously uses the image information and spectral information of the part of human body to be detected, which improves the accuracy and safety of blood glucose detection. At the same time, the chip partially implements an artificial neural network on the hardware, which improves the speed of blood glucose detection. In addition, the solution of the chip may use the traditional CMOS process to achieve mass production, reducing the volume, power consumption and cost of the device.

Further, the optical modulation structure in the optical filter layer includes a regular structure and/or an irregular structure; and/or, the optical modulation structure in the optical filter layer includes a discrete structure and/or a continuous structure.

Further, the optical filter layer has a single-layer structure or a multi-layer structure.

Further, the optical modulation structure in the optical filter layer includes a unit array composed of a plurality of micro-nano units, and each micro-nano unit corresponds to one or more pixels on the image sensor; each micro-nano unit has the same or different structure.

Further, the micro-nano unit includes a regular structure and/or an irregular structure; and/or the micro-nano unit includes a discrete structure and/or a continuous structure.

Further, the micro-nano unit includes a plurality of groups of micro-nano structure arrays, and each group of the micro-nano structure arrays has the same or different structure.

Further, each group of micro-nano structure array has the broadband filtering or narrowband filtering functions.

Further, each group of micro-nano structure arrays is a periodic structure array or an aperiodic structure array.

Further, one or more of the plurality of groups of micro-nano structure arrays contained in the micro-nano unit has empty structures.

Further, the micro-nano unit has polarization-independent characteristics.

Further, the micro-nano unit has four-fold rotation symmetry.

Further, the optical filter layer is composed of one or more filter layers;

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

Further, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nanopillar two-dimensional materials, and nanowire two-dimensional materials.

Further, the optical filter layer has a thickness of $0.1\lambda$-$10\lambda$, where $\lambda$ represents the center wavelength of the incident light.

An embodiment of the present application also provides an intelligent blood glucose detector, including the optical artificial neural network blood glucose detection chip described in the above embodiment, and the blood glucose detector may be a wearable blood glucose detector. Since the intelligent blood glucose detector has similar beneficial effects as the aforementioned optical artificial neural network blood glucose detection chip, it will not be repeated here.

An embodiment of the present application also provides a method for preparing the optical artificial neural network blood glucose detection chip as described above, including:
preparing an optical filter layer containing an optical modulation structure on a surface of a photosensitive area of an image sensor;
generating a processor with the functions of fully connected processing and nonlinear activation processing of signals; and
connecting the image sensor and the processor;
wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and
the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain blood glucose detection results; and the electrical signals are image signals modulated by the optical filter layer and the incident light includes reflected light and/or transmitted light of a part of the human body to be detected.

Further, the method for preparing the optical artificial neural network blood glucose detection chip further includes a training process of the optical artificial neural network blood glucose detection chip and specifically includes:
training the optical artificial neural network blood glucose detection chip containing different optical modulation structures, image sensors, and processors with different fully connected parameters and different nonlinear activation parameters using input training samples and output training samples corresponding to the blood glucose detection task to obtain an optical modulation structure, an image sensor and an processor satisfying the training convergence condition and taking the optical modulation structure, the image sensor and the processor satisfying the training convergence condition as the trained optical modulation structure, the image sensor and the processor.

Further, when the optical artificial neural network blood glucose detection chip containing different optical modulation structures, image sensors, and processors with different fully connected parameters and nonlinear activation parameters is trained, the different optical modulation structures are designed and implemented in a computer optical simulation design manner.

It should be noted that the optical artificial neural network blood glucose detection chip based on the micro-nano modulation structure and the image sensor according to this embodiment has the following effects: A. the artificial neural network is partially embedded in the image sensor containing various optical filter layers to provide safe, reliable, fast and accurate noninvasive blood glucose detection. B. The preparation of the chip can be completed one time by the CMOS process, which is beneficial to decrease the failure rate of the device, improve the yield of the device, and reduce the cost. C. Implement of monolithic integration at a wafer level may minimize the distance between the sensor and the optical filter layer, which is conducive to decreasing the size of the unit, reducing the volume of the device and the packaging cost.

It should be noted that for the detailed structural description of the optical artificial neural network blood glucose detection chip according to this embodiment, reference may be made to the description of the optical artificial neural network chip in the foregoing embodiments, and in order to avoid repetitive description, it will not be described here. In addition, for the detailed description of the preparation method of the optical artificial neural network blood glucose detection chip, reference may also be made to the description of the preparation method of the optical artificial neural network intelligent chip in the foregoing embodiment, which will not be repeated here.

Precision agriculture is a system supported by information technology to timely and quantitatively implement a complete set of modern agricultural operation technology and management based on spatial variation. The basic meaning of the precision agriculture is, in one hand, to adjust the input of crops and judge properties of soil inside the farmland and spatial variation of productivity according to the properties of soil in which crops grow, on the other hand, to determine the production target of crops, carry out orientated "system diagnosis, optimized formula, technical assembly, scientific management", mobilize soil productivity, and achieve the same income or higher income with the least or most economical input, improve environment, efficiently use various agricultural resources, and achieve economic and environmental benefits.

At present, when precision agriculture control is performed, there are problems of slow processing speed and inaccurate recognition. For example, for the recognition of soil fertility, image collection, image preprocessing, feature extraction, feature matching and other steps are required to provide the recognition of soil fertility. However, it is currently difficult to ensure the accuracy of recognition using only the two-dimensional image information of soils, for example, there are distortion factors in the two-dimensional image. Also, during the imaging process, optical information needs to be converted into digital electronic signals, and then transmitted to a computer for subsequent algorithm processing. Therefore, the transmission and processing of a large amount of data causes greater power consumption and delay. In addition, similar problems exist in the recognition of crop growth conditions.

The technical principle of precision agriculture is to adjust the input of crops according to soil fertility and the spatial difference of crop growth conditions. When the recognition of soil fertility and crop growth conditions is inaccurate, and there is a large power consumption and time delay, it will seriously affect the development of precision agriculture.

To this end, based on the optical artificial neural network intelligent chip described in the previous embodiment, the present embodiment provides a new optoelectronic chip for agricultural precision control intelligent processing tasks. In the optoelectronic chip, the optical filter layer constitutes the input layer and the connection weight from the input layer to the linear layer of the optical artificial neural network; and the image sensors constitutes the linear layer of the optical artificial neural network. By collecting the image information and spectral information of the soil and crops in the farmland, the fast, accurate, safe and reliable recognition and qualitative analysis of soil fertility and pesticide spreading condition, trace element content and crop growth status may be provided. The present embodiment will be specifically explained and described in detail below.

An embodiment of the present application also provides an optical artificial neural network intelligent agricultural precision control chip for agricultural precision control intelligent processing tasks, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; the incident light includes reflected light, transmitted light and/or radiated light of an agricultural object; and the agricultural object includes crops and/or soil;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer; and the processor is configured to perform fully connected processing and nonlinear activation processing on the electrical signals corresponding to the different location points to obtain agricultural precision control processing results; and the agricultural precision control intelligent processing tasks include one or more of detection of soil fertility, detection of pesticide spreading, detection of trace element content, detection of pesticide resistance, and detection of crop growth status; and the agricultural precision control processing results include one or more of detection results of soil fertility, detection results of pesticide spreading, detection results of trace element content, detection results of pesticide resistance, and detection results of crop growth status.

The present embodiment provides a new optical artificial neural network intelligent agricultural precision control chip capable of implementing artificial neural network functions, which is used for agricultural precision control intelligent processing tasks. In the embodiment of the present application, the artificial neural network is embedded in the hardware chip, and the optical filter layer on the hardware chip serves as the input layer and the connection weight from the input layer to the linear layer of the artificial neural network. The image sensor on the hardware chip serves as the linear layer of the artificial neural network. The spatial spectrum information of soil and crops in the farmland is incident on the pre-trained hardware chip, and the artificial neural network analysis is performed on the spatial spectrum information of the soil and crops in the farmland by hardware chip to obtain the agricultural precision control processing result. It should be noted that low power consumption and safe, reliable, fast and accurate recognition and qualitative analysis of soil fertility and pesticide spreading condition, trace element content and crop growth status is provided in the embodiment of the present application.

It may be understood that in the optical artificial neural network intelligent agricultural precision control chip, an optical filter layer, that is a hardware structure thereon corresponds to an input layer and a connection weight from the input layer to a linear layer of an artificial neural network; the image sensor, that is a hardware structure thereon corresponds to the linear layer of the artificial neural network; and the processor corresponds to a nonlinear layer and an output layer of the artificial neural network. Specifically, the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area through the optical modulation structure. Accordingly, the image sensor is configured to convert the information carried in the incident light corresponding to different location points after being modulated by the optical filter layer into electric signals corresponding to the different location points, and at the same time, the processor connected with the image sensor is configured to perform fully connected processing and nonlinear activation processing on the electrical signals corresponding to the different location points to obtain output signals of the artificial neural network. In the intelligent agricultural precision control chip, the optical filter layer serves as the input layer of the artificial neural network, the image sensor serves as the linear layer of the artificial neural network. At the same time, the filtering effect of the optical filter layer on the incident light entering the optical filter layer corresponds to the connection weight from the input layer to the linear layer, that is, the optical filter layer and the image sensor of the intelligent agricultural precision control chip provide related functions of the input layer and the linear layer in the artificial neural network. That is, in the embodiment of the present application, the input layer and the linear layer in the artificial neural network implemented by software are stripped and the two-layer structure of the input layer and the linear layer in the artificial neural network is implemented by hardware, so that no complicated signal processing and algorithm processing corresponding to the input layer and the linear layer need to be performed in the subsequent artificial neural network intelligent processing using the intelligent agricultural precision control chip and the processor in the intelligent agricultural precision control chip only needs to perform fully connected processing and nonlinear activation processing on the electrical signals, which may greatly reduce the power consumption and delay of artificial neural network intelligent agricultural precision control. In the embodiment of the present application, the optical filter layer serves as the input layer of the artificial neural network, the image sensor serves as the linear layer of the artificial neural network, the filtering effect of the optical filter layer on the incident light entering the optical filter layer serves as the connection weight from the input layer to the linear layer; spatial spectral information of soil and crops in the farmland is projected into electrical signals using the optical filter layer and the image sensor and the fully connected processing and nonlinear activation processing on the electrical signals are then implemented in the processor. Also, in the embodiment of the present application, the complicated signal processing and algorithm processing corresponding to the input layer and linear layer may not only be omitted and the image information of the soil and crops in the farmland, spectral information, angle information of the incident light and phase information of the incident light, that is, the information carried by the incident light at different points in the soil and crop spaces in the farmland may but also actually simultaneously utilized. Since the information carried by the incident light at different points in the soil and crop spaces in the farmland covers information of the soil and crop spaces in the farmland such as images, composition, shape, three-dimensional depth, structure and the like, the information of the soil and crop spaces in the farmland such as images, composition, shape, three-dimensional depth, structure and the like is covered when the recognition processing is performed according to the information carried by the incident light at different points in the soil and crop spaces in the farmland, such that fast, accurate, safe and reliable recognition and qualitative analysis of soil fertility and pesticide spreading condition, trace element content and crop growth status may be performed accurately.

Further, the optical artificial neural network intelligent agricultural precision control chip includes a trained optical modulation structure, an image sensor and a processor;

the trained optical modulation structure, an image sensor and a processor refer to an optical modulation structure, an image sensor and an processor satisfying the training convergence condition obtained by training the optical artificial neural network intelligent agricultural precision control chip containing different optical modulation structures, image sensors, and processors with different fully connected parameters and different nonlinear activation parameters using input training samples and output training samples corresponding to agricultural precision control intelligent processing tasks;

in an embodiment, the input training samples include incident light reflected, transmitted and/or radiated by soils with different fertilities; the output training samples include corresponding soil fertilities; and/or, the input training samples include incident light reflected, transmitted and/or radiated by soils with different pesticide spreading conditions; the output training samples include corresponding pesticide spreading conditions; and/or, the input training samples include incident light reflected, transmitted and/or radiated by soils with different trace element content conditions; the output training samples include corresponding trace element content conditions; and/or, the input training samples include incident light reflected, transmitted and/or radiated by soils with different pesticide resistances; the output training samples include corresponding drug resistances; and/or, the input training samples include incident light reflected, transmitted and/or radiated by crops with different growth conditions; the output training samples include corresponding crop growth conditions.

Further, when the optical artificial neural network intelligent agricultural precision control chip containing different optical modulation structures, image sensors, and processors with different fully connected parameters and nonlinear activation parameters is trained, the different optical modulation structures are designed and implemented in a computer optical simulation design manner.

In this embodiment, for agricultural precision control processing task, a large number of soil samples and crop samples with different states at different positions may be collected first, and the weights from the input layer to the linear layer, that is, a system function of the optical filter layer may be obtained through data training. The required optical filter layer may be reversely designed and the designed optical filter layer is integrated above the image sensor. In actual training, the weight of the electrical signal fully connected layer is further trained and optimized using the soil samples and crop samples and the output of the completed optical filter layer to implement a high-accuracy optical artificial neural network and thus recognition and qualitative analysis of soil fertility and pesticide spreading condition, trace element content and crop growth status are completed.

It may be understood that the specific modulation pattern of the modulation structure on the optical filter layer is obtained by collecting a large number of soil samples and crop samples with different states at different positions in the early stage, and is designed by artificial neural network data training. The modulation pattern usually has an irregularly shaped structure, of course, it may also have regularly shaped structure.

Figure 19:
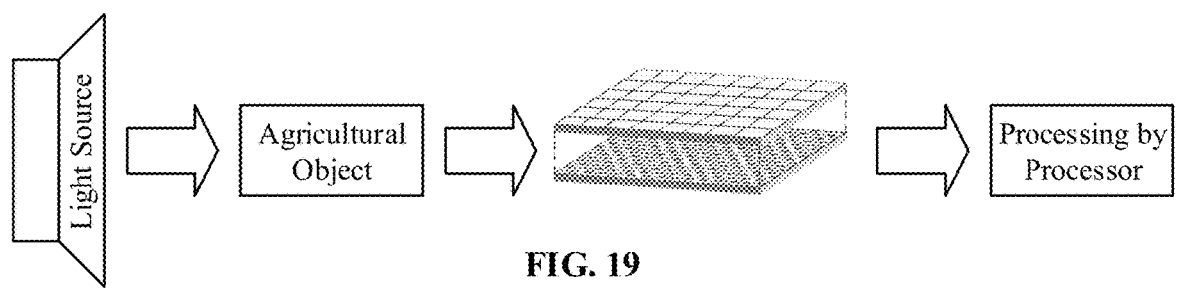
FIG. 19 is a schematic diagram of a process of recognizing agricultural objects according to an exemplary embodiment of the present application.
Figure 20:
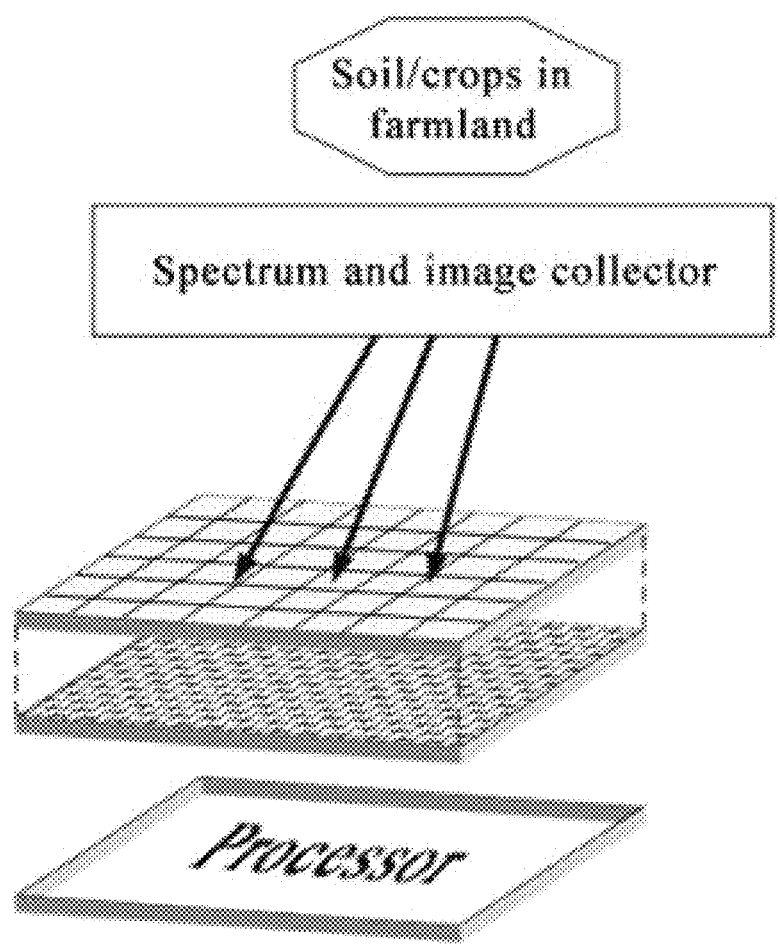
FIG. 20 is a perspective schematic diagram of recognizing or qualitatively analyzing crops and/or soil according to an exemplary embodiment of the present application.

As shown in FIG. 19, the complete process for an agricultural object recognition includes allowing ambient light or other light sources to irradiate then agricultural object, collecting the reflected light by the chip, and internally processing the reflected light to obtain the recognition result. As shown in FIG. 20, the spectral data and images of soil and crops in the farmland are collected by the spectrum and image collector, and then the reflected light is collected by the precision agriculture control chip, and then processed by the internal algorithm of the processor to obtain the recognition results.

It may be understood that the chip actually uses image information and spectral information of soil and crops in the farmland at the same time to provide safe, reliable, fast and accurate precision agriculture control. In addition, the solution of the chip may use the traditional CMOS process to achieve mass production, reducing the volume, power consumption and cost of the device.

Further, the optical modulation structure in the optical filter layer includes a regular structure and/or an irregular structure; and/or, the optical modulation structure in the optical filter layer includes a discrete structure and/or a continuous structure.

Further, the optical filter layer has a single-layer structure or a multi-layer structure.

Further, the optical modulation structure in the optical filter layer includes a unit array composed of a plurality of micro-nano units, and each micro-nano unit corresponds to one or more pixels on the image sensor; each micro-nano unit has the same or different structure.

Further, the micro-nano unit includes a regular structure and/or an irregular structure; and/or the micro-nano unit includes a discrete structure and/or a continuous structure.

Further, the micro-nano unit includes a plurality of groups of micro-nano structure arrays, and each group of the micro-nano structure arrays has the same or different structure.

Further, each group of micro-nano structure array has the broadband filtering or narrowband filtering functions.

Further, each group of micro-nano structure arrays is a periodic structure array or an aperiodic structure array.

Further, one or more of the plurality of groups of micro-nano structure arrays contained in the micro-nano unit has empty structures.

Further, the micro-nano unit has polarization-independent characteristics.

Further, the micro-nano unit has four-fold rotation symmetry.

Further, the optical filter layer is composed of one or more filter layers;

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

Further, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nano-pillar two-dimensional materials, and nanowire two-dimensional materials.

Further, the optical filter layer has a thickness of $0.1\lambda$-$10\lambda$, where $\lambda$ represents the center wavelength of the incident light.

An embodiment of the present application also provides an intelligent agricultural control apparatus, including the optical artificial neural network intelligent agricultural precision control chip as described in above embodiments. The intelligent agricultural control apparatus may include a fertilizer applicator, a pesticide spreader, a pesticide resistance analyzer, an unmanned aerial vehicle, an agricultural intelligent robot, a crop health analyzer, a crop growth state monitoring apparatus, and the like.

Another embodiment of the present application also provides a method for preparing the optical artificial neural network intelligent agricultural precision control chip as described in above embodiment, including:
    preparing an optical filter layer containing an optical modulation structure on a surface of a photosensitive area of an image sensor;
    generating a processor with the functions of fully connected processing and nonlinear activation processing of signals; and
    connecting the image sensor and the processor;
    wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and
    the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain agricultural precision control results; and the electrical signals are image signals modulated by the optical filter layer and the incident light includes reflected light, transmitted light and/or radiated light of an agricultural object; the agricultural object includes crops and/or soil.

Further, the method for preparing the optical artificial neural network intelligent agricultural precision control chip further includes a training process of the optical artificial neural network intelligent agricultural precision control chip and specifically includes:
    training the optical artificial neural network intelligent agricultural precision control chip containing different optical modulation structures, image sensors, and processors with different fully connected parameters and different nonlinear activation parameters using input training samples and output training samples corresponding to the agricultural precision control intelligent processing tasks to obtain an optical modulation structure, an image sensor and an processor satisfying the training convergence condition and taking the optical modulation structure, the image sensor and the processor satisfying the training convergence condition as the trained optical modulation structure, the image sensor and the processor.

Further, when the optical artificial neural network intelligent agricultural precision control chip containing different optical modulation structures, image sensors, and processors with different fully connected parameters and nonlinear activation parameters is trained, the different optical modulation structures are designed and implemented in a computer optical simulation design manner.

It should be noted that the optical artificial neural network intelligent agricultural precision control chip based on the micro-nano modulation structure and the image sensor according to the present embodiment has the following effects: A. the artificial neural network is partially embedded in the image sensor containing various optical filter layers to provide safe, reliable, fast and accurate agricultural precision control. B. Artificial neural networks may be introduced for training and recognition of soil and crops, which is convenient for being subsequently integrated into industrial intelligent control systems such as unmanned aerial vehicles and intelligent robots to achieve precise agricultural control in a large area, with high recognition accuracy and accurate qualitative analysis. C. The preparation of the chip can be completed one time by the CMOS process, which is beneficial to decrease the failure rate of the device, improve the yield of the device, and reduce the cost. D. Implement of monolithic integration at a wafer level may minimize the distance between the sensor and the optical filter layer, which is conducive to decreasing the size of the unit, reducing the volume of the device and the packaging cost.

It should be noted that for the detailed structural description of the optical artificial neural network intelligent agricultural precision control chip according to the present embodiment, reference may be made to the description of the optical artificial neural network intelligent chip in the foregoing embodiment, and in order to avoid repetitive description, it will not be described here. In addition, for the detailed description of the preparation method of the optical artificial neural network intelligent agricultural precision control chip, reference may also be made to the description of the preparation method of the optical artificial neural network intelligent chip in the foregoing embodiment, which will not be repeated here.

Converter steelmaking is currently the most widely used and most efficient steelmaking method in the world. Smelting endpoint control is one of the key technologies in converter production. It is of great significance for the curate judgment of the endpoint in terms of improving the quality of molten steel and shortening the smelting cycle. However, due to the unstable raw materials entering the furnace, complex chemical reactions and strict steel types, it is still difficult to accurately control the smelting endpoint. Accurate online detection of carbon content and molten steel temperature at the endpoint has always been a problem to be solved in the metallurgical industry all over the world. At present, the endpoint control in the industry mainly relies on manual experience, or the qualitative measurement of furnace mouth temperature and slag residue by complex large instruments and equipment has the disadvantages of low accuracy and high cost.

To this end, based on the optical artificial neural network intelligent chip described in the previous embodiment, the present embodiment provides a new optoelectronic chip for smelting endpoint monitoring. In the optoelectronic chip, the optical filter layer constitutes the input layer and the connection weight from the input layer to the linear layer of the optical artificial neural network; and the image sensors constitutes the linear layer of the optical artificial neural network. By collecting the image information and spectral information of the steel furnace mouth, fast, accurate, safe and reliable recognition of the smelting endpoint may be provided. The present embodiment will be specifically explained and described in detail below.

An embodiment of the present application also provides an optical artificial neural network smelting endpoint monitoring chip for smelting endpoint monitoring tasks, including: an optical filter layer, an image sensor, and a processor; the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;

the optical filter layer is disposed on the surface of a photosensitive area of the image sensor, the optical filter layer includes an optical modulation structure, and is configured to modulate, with different spectra incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and the incident light includes reflected light, transmitted light and/or radiated light at a mouth of a steel-making furnace;

the image sensor is configured to convert information carried in the incident light corresponding to different location points after being modulated by the optical filter layer into electric signals corresponding to the different location points, and send the electric signals corresponding to the different location points to the processor and the electrical signals are image signals modulated by the optical filter layer; and the processor is configured to perform fully connected processing and nonlinear activation processing on the electrical signals corresponding to the different location points to obtain smelting endpoint monitoring results.

In an embodiment, the smelting endpoint monitoring tasks include recognition of the smelting endpoint, and the smelting endpoint monitoring result includes the smelting endpoint recognition result.

The present embodiment provides a new optical artificial neural network smelting endpoint monitoring chip capable of implementing artificial neural network functions, which is used for smelting endpoint monitoring tasks. In the embodiment of the present application, the artificial neural network is embedded in the hardware chip, and the optical filter layer on the hardware chip serves as the input layer and the connection weight from the input layer to the linear layer of the artificial neural network. The image sensor on the hardware chip serves as the linear layer of the artificial neural network. The spatial spectrum information of the steel-making furnace mouth is incident on the pre-trained hardware chip, and the artificial neural network analysis is performed on the spatial spectrum information of the steel-making furnace mouth by hardware chip to obtain the smelting endpoint monitoring result. It should be noted that low power consumption and safe, reliable, fast and accurate smelting endpoint monitoring is provided in the embodiment of the present application.

It may be understood that in the optical artificial neural network smelting endpoint monitoring chip, an optical filter layer, that is a hardware structure thereon corresponds to an input layer and a connection weight from the input layer to a linear layer of an artificial neural network; the image sensor, that is a hardware structure thereon corresponds to the linear layer of the artificial neural network; and the processor corresponds to a nonlinear layer and an output layer of the artificial neural network. Specifically, the optical filter layer is disposed on the surface of a photosensitive area of the image sensor, the optical filter layer includes an optical modulation structure, and is configured to modulate, with different spectra, incident light which is incident to different location points of the optical modulation structure respectively by the optical modulation structure, to obtain information carried in the incident light corresponding to different location points on the surface of the photosensitive area through the optical modulation structure. Accordingly, the image sensor is configured to convert the information carried in the incident light corresponding to different location points after being modulated by the optical filter layer into electric signals corresponding to the different location points, and at the same time, the processor connected with the image sensor is configured to perform fully connected processing and nonlinear activation processing on the electrical signals corresponding to the different location points to obtain output signals of the artificial neural network. In the smelting endpoint monitoring chip, the optical filter layer serves as the input layer of the artificial neural network, the image sensor serves as the linear layer of the artificial neural network. At the same time, the filtering effect of the optical filter layer on the incident light entering the optical filter layer corresponds to the connection weight from the input layer to the linear layer, that is, the optical filter layer and the image sensor of the smelting endpoint monitoring chip provide related functions of the input layer and the linear layer in the artificial neural network. That is, in the embodiment of the present application, the input layer and the linear layer in the artificial neural network implemented by software are stripped and the two-layer structure of the input layer and the linear layer in the artificial neural network is implemented by hardware, so that no complicated signal processing and algorithm processing corresponding to the input layer and the linear layer need to be performed in the subsequent artificial neural network smelting endpoint recognition processing using the smelting endpoint monitoring chip and the processor in the smelting endpoint monitoring chip only needs to perform fully connected processing and nonlinear activation processing on the electrical signals, which may greatly reduce the power consumption and delay of artificial neural network smelting endpoint monitoring. In the embodiment of the present application, the optical filter layer serves as the input layer of the artificial neural network, the image sensor serves as the linear layer of the artificial neural network, the filtering effect of the optical filter layer on the incident light entering the optical filter layer serves as the connection weight from the input layer to the linear layer; spatial spectral information of a steel-making furnace mouth is projected into electrical signals using the optical filter layer and the image sensor and the fully connected processing and nonlinear activation processing on the electrical signals are then implemented in the processor. Also, in the embodiment of the present application, the complicated signal processing and algorithm processing corresponding to the input layer and linear layer may not only be omitted and the image information of the steel-making furnace mouth, spectral information, angle information of the incident light and phase information of the incident light, that is, the information carried by the incident light at different points in the steel-making furnace mouth space may but also actually simultaneously utilized. Since the information carried by the incident light at different points in the steel-making furnace mouth space covers information of the steel-making furnace mouth such as images, composition, shape, three-dimensional depth, structure and the like, the information of the steel-making furnace mouth such as images, composition, shape, three-dimensional depth, structure and the like is covered when the recognition processing is performed according to the information carried by the incident light at different points in the steel-making furnace mouth space, such that smelting endpoint recognition may be performed accurately.

Further, the smelting endpoint monitoring tasks further include recognition of a carbon content and/or molten steel temperature during the smelting process, and the smelting endpoint monitoring result includes the carbon content and/or molten steel temperature recognition result during the smelting process.

Further, the optical artificial neural network smelting endpoint monitoring chip includes a trained optical modulation structure, an image sensor and a processor;

the trained optical modulation structure, an image sensor and a processor refer to an optical modulation structure, an image sensor and an processor satisfying the training convergence condition obtained by training the optical artificial neural network smelting endpoint monitoring chip containing different optical modulation structures, image sensors, and processors with different fully connected parameters and different nonlinear activation parameters using input training samples and output training samples corresponding to the smelting endpoint monitoring tasks; and the input training samples include incident light reflected, transmitted, and/or radiated at the mouth of the steel-making furnace when the smelting endpoint is arrived and when the smelting endpoint is not arrived; the output training samples include the determination result that whether the smelting endpoint is arrived.

Further, when the smelting endpoint monitoring task also includes recognition of a carbon content and/or molten steel temperature during the smelting process, correspondingly, the input training sample also includes incident light reflected, transmitted, and/or radiated at the mouth of the steel-making furnace when different carbon contents and/or molten steel temperature are obtained while smelting and the output training sample also includes the corresponding carbon content and/or molten steel temperature.

Further, when the optical artificial neural network smelting endpoint monitoring chip containing different optical modulation structures, image sensors, and processors with different fully connected parameters and nonlinear activation parameters is trained, the different optical modulation structures are designed and implemented in a computer optical simulation design manner.

In this embodiment, for smelting endpoint recognition, images and spectral information of a large number of converter furnace mouths at the end point may be collected first, and the weights from the input layer to the linear layer, that is, a system function of the optical filter layer may be obtained through data training. The required optical filter layer may be reversely designed and the designed optical filter layer is integrated above the image sensor. In actual training, the weight of the electrical signal fully connected layer is further trained and optimized using converter furnace mouth samples to be recognized and the output of the completed optical filter layer to implement a high-accuracy optical artificial neural network and thus fast and accurate recognition of the smelting endpoint is completed.

It may be understood that the specific modulation pattern of the modulation structure on the optical filter layer is obtained by collecting images and spectral information of a large number of converter furnace mouths at the end point in the early stage, and is designed by artificial neural network data training. The modulation pattern usually has an irregularly shaped structure, of course, it may also have regularly shaped structure.

Figure 21:
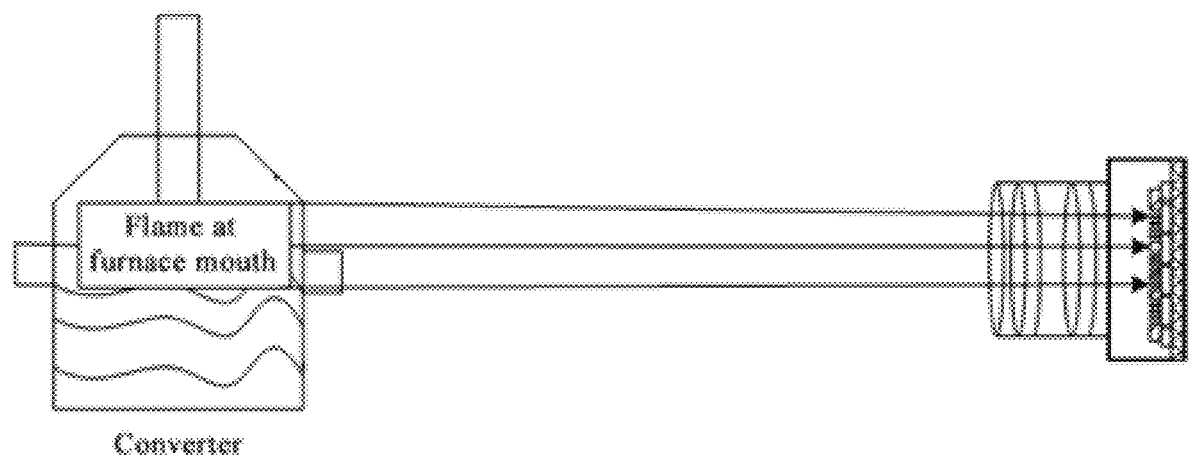
FIG. 21 is a schematic diagram of recognizing a furnace mouth during the smelting process to determine a smelting endpoint according to an exemplary embodiment of the present application.

As shown in FIG. 21, the complete process of recognizing the steel-making furnace mouth to determine whether it is the smelting endpoint includes allowing ambient light or other light sources to irradiate the steel-making furnace mouth, collecting the reflected light by the chip, and internally processing the reflected light to obtain the recognition result.

It may be understood that the chip actually simultaneously uses the image information and spectral information of the steel-making furnace mouth, which improves the accuracy and safety of smelting endpoint recognition. At the same time, the chip partially implements an artificial neural network on the hardware, which improves the speed of smelting endpoint recognition. In addition, the solution of the chip may use the traditional CMOS process to achieve mass production, reducing the volume, power consumption and cost of the device.

Further, the optical modulation structure in the optical filter layer includes a regular structure and/or an irregular structure; and/or, the optical modulation structure in the optical filter layer includes a discrete structure and/or a continuous structure.

Further, the optical filter layer has a single-layer structure or a multi-layer structure.

Further, the optical modulation structure in the optical filter layer includes a unit array composed of a plurality of micro-nano units, and each micro-nano unit corresponds to one or more pixels on the image sensor; each micro-nano unit has the same or different structure.

Further, the micro-nano unit includes a regular structure and/or an irregular structure; and/or the micro-nano unit includes a discrete structure and/or a continuous structure.

Further, the micro-nano unit includes a plurality of groups of micro-nano structure arrays, and each group of the micro-nano structure arrays has the same or different structure.

Further, each group of micro-nano structure array has the broadband filtering or narrowband filtering functions.

Further, each group of micro-nano structure arrays is a periodic structure array or an aperiodic structure array.

Further, one or more of the plurality of groups of micro-nano structure arrays contained in the micro-nano unit has empty structures.

Further, the micro-nano unit has polarization-independent characteristics.

Further, the micro-nano unit has four-fold rotation symmetry.

Further, the optical filter layer is composed of one or more filter layers;

The filter layer is prepared from one or more of semiconductor materials, metal materials, liquid crystals, quantum dot materials, and perovskite materials; and/or, the filter layer is a filter layer prepared from one or more of photonic crystals, metasurfaces, random structures, nanostructures, metal surface plasmon SPP micro-nano structure, and a tunable Fabry-Perot resonant cavity.

Further, the semiconductor materials include one or more of silicon, silicon oxide, silicon nitride, titanium oxide, a composite material mixed in a preset ratio and direct-gap semiconductor materials; and/or, the nanostructure includes one or more of nanodot two-dimensional materials, nanopillar two-dimensional materials, and nanowire two-dimensional materials.

Further, the optical filter layer has a thickness of $0.1\lambda$-$10\lambda$, where $\lambda$ represents the center wavelength of the incident light.

An embodiment of the present application also provides an intelligent smelting control apparatus, including the optical artificial neural network smelting endpoint monitoring chip as described in above embodiment. The intelligent smelting control apparatus may include various apparatuses related to smelting process control, which is not limited in present embodiment. The intelligent smelting control apparatus provided in present embodiment has all the beneficial effects of the optical artificial neural network smelting endpoint monitoring chip described in the above embodiment. Since the above embodiment has already described this in more detail, it will not be repeated in present embodiment.

An embodiment of the present application also provides a method for preparing the optical artificial neural network smelting endpoint monitoring chip as described above, including:

preparing an optical filter layer containing an optical modulation structure on a surface of a photosensitive area of an image sensor;

generating a processor with the functions of fully connected processing and nonlinear activation processing of signals; and connecting the image sensor and the processor;

wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light includes light intensity distribution information, spectral information, angle information of the incident light and phase information of the incident light; and the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain smelting endpoint monitoring results; and the electrical signals are image signals modulated by the optical filter layer and the incident light includes reflected light, transmitted light and/or radiated light at a mouth of a steel-making furnace.

Further, the method for preparing the optical artificial neural network smelting endpoint monitoring chip further includes a training process of the optical artificial neural network smelting endpoint monitoring chip and specifically includes:

training the optical artificial neural network smelting endpoint monitoring chip containing different optical modulation structures, image sensors, and processors with different fully connected parameters and different nonlinear activation parameters using input training samples and output training samples corresponding to the smelting endpoint monitoring tasks to obtain an optical modulation structure, an image sensor and an processor satisfying the training convergence condition and taking the optical modulation structure, the image sensor and the processor satisfying the training convergence condition as the trained optical modulation structure, the image sensor and the processor.

Further, when the optical artificial neural network smelting endpoint monitoring chip containing different optical modulation structures, image sensors, and processors with different fully connected parameters and nonlinear activation parameters is trained, the different optical modulation structures are designed and implemented in a computer optical simulation design manner.

It should be noted that the optical artificial neural network intelligent smelting endpoint monitoring chip based on the micro-nano modulation structure and the image sensor according to the present embodiment has the following effects: A. the artificial neural network is partially embedded in the image sensor containing various optical filter layers to provide safe, reliable, fast and accurate smelting endpoint control. B. Detectable samples include but are not limited to the converter steelmaking endpoint control. Artificial neural network training is introduced to detect the temperature and material elements of the smelting furnace mouth which is very easy to integrate back-end industrial control systems, and has high recognition accuracy and accurate qualitative analysis. C. The preparation of the chip can be completed one time by the CMOS process, which is beneficial to decrease the failure rate of the device, improve the yield of the device, and reduce the cost. D. Implement of monolithic integration at a wafer level may minimize the distance between the sensor and the optical filter layer, which is conducive to decreasing the size of the unit, reducing the volume of the device and the packaging cost.

It should be noted that for the detailed structural description of the optical artificial neural network intelligent smelting endpoint monitoring chip according to the present embodiment, reference may be made to the description of the optical artificial neural network intelligent chip in the foregoing embodiment, and in order to avoid repetitive description, it will not be described here. In addition, for the detailed description of the preparation method of the optical artificial neural network smelting endpoint monitoring chip, reference may also be made to the description of the preparation method of the optical artificial neural network intelligent chip in the foregoing embodiment, which will not be repeated here.

Finally, it should be noted that the above-described exemplary embodiments are only used to explain the technical solutions of the present application, but are not limited thereto; although the present application is described in detail with reference to the foregoing embodiments, it should be understood by those skilled in the art that they can still modify the technical solutions described in the foregoing embodiments and make equivalent substitutions to a part of the technical features and these modifications and substitutions do not depart from the scope of the technical solutions of the embodiments of the present application.

The invention claimed is:

1. An optical artificial neural network intelligent chip, comprising:
    an optical filter layer,
    an image sensor, and
    a processor;
    wherein the optical filter layer corresponds to an input layer and a connection weight from the input layer to a linear layer of an artificial neural network; the image sensor corresponds to the linear layer of the artificial neural network; and the processor corresponds to a nonlinear layer and an output layer of the artificial neural network;
    the optical filter layer is disposed on the surface of a photosensitive area of the image sensor, the optical filter layer comprises an optical modulation structure, and is configured to modulate, with different spectra, incident light which is incident to different location points of the optical modulation structure respectively by the optical modulation structure, to obtain information carried in the incident light corresponding to different location points on the surface of the photosensitive area; the information carried in the incident light comprises light intensity distribution information, spectral information, angle information of the incident light and phase information of the incident light;
    the image sensor is configured to convert information carried in the incident light corresponding to different location points after being modulated by the optical filter layer into electric signals corresponding to the different location points, and send the electric signals corresponding to the different location points to the processor, wherein the electrical signals are image signals modulated by the optical filter layer; and
    the processor is configured to perform fully connected processing and nonlinear activation processing on the electrical signals corresponding to the different location points to obtain output signals of the artificial neural network.

2. The optical artificial neural network intelligent chip of claim 1, wherein the optical artificial neural network intelligent chip is used for intelligent processing tasks of a target object; the intelligent processing tasks comprise at least one or more of an intelligent perception task, an intelligent recognition task and an intelligent decision task;
    reflected light, transmitted light and/or radiation light of the target object enters a trained optical artificial neural network intelligent chip to obtain intelligent processing results of the target object; the intelligent processing results comprise at least one or more of an intelligent perception result, an intelligent recognition result and/or an intelligent decision result;
    wherein the trained optical artificial neural network intelligent chip refers to an optical artificial neural network intelligent chip including a trained optical modulation structure, an image sensor and a processor; the trained optical modulation structure, the image sensor and the processor refer to an optical modulation structure, an image sensor and an processor satisfying a training convergence condition obtained by training the optical artificial neural network intelligent chip containing different optical modulation structures, image sensors, and processors with different fully connected parameters and nonlinear activation parameters using input training samples and output training samples corresponding to the intelligent processing task.

3. The optical artificial neural network intelligent chip of claim 2, wherein when the optical artificial neural network intelligent chip containing different optical modulation structures, image sensors, and processors with different fully connected parameters and nonlinear activation parameters is trained, the different optical modulation structures are designed and implemented in a computer optical simulation design manner.

4. The optical artificial neural network intelligent chip of claim 1, wherein the optical modulation structure in the optical filter layer comprises a regular structure and/or an irregular structure; and/or, the optical modulation structure in the optical filter layer comprises a discrete structure and/or a continuous structure.

5. The optical artificial neural network intelligent chip of claim 1, wherein the optical filter layer has a single-layer structure or a multi-layer structure.

6. The optical artificial neural network intelligent chip of any one of claims 1 to 3, wherein the optical modulation structure in the optical filter layer comprises a unit array composed of a plurality of micro-nano units, and each micro-nano unit corresponds to one or more pixels on the image sensor; each micro-nano unit has the same or different structure.

7. The optical artificial neural network intelligent chip of claim 6, wherein the micro-nano unit comprises a regular structure and/or an irregular structure; and/or, the micro-nano unit comprises a discrete structure and/or a continuous structure.

8. The optical artificial neural network intelligent chip of claim 6, wherein the micro-nano unit comprises a plurality of groups of micro-nano structure arrays, and each group of the micro-nano structure arrays has the same or different structure.

9. The optical artificial neural network intelligent chip of claim 8, wherein each group of micro-nano structure array has broadband filtering or narrowband filtering functions.

10. The optical artificial neural network intelligent chip of claim 8, wherein each group of micro-nano structure arrays is a periodic structure array or an aperiodic structure array.

11. The optical artificial neural network intelligent chip of claim 8, wherein the plurality of groups of micro-nano structure arrays contained in the micro-nano unit has one or more groups of empty structures.

12. The optical artificial neural network intelligent chip of claim 8, wherein the micro-nano unit has polarization-independent characteristics.

13. The optical artificial neural network intelligent chip of claim 12, wherein the micro-nano unit has four-fold rotation symmetry.

14. The optical artificial neural network intelligent chip of claim 1, wherein the optical filter layer is composed of one or more filter layers;
the filter layer is prepared from one or more of semiconductor materials, metal materials, liquid crystals, quantum dot materials, and perovskite materials; and the filter layer is a filter layer prepared from one or more of photonic crystals, metasurfaces, random structures, nanostructures, metal surface plasmon SPP micro-nano structure, and a tunable Fabry-Perot resonant cavity.

15. The optical artificial neural network intelligent chip of claim 14, wherein the semiconductor materials comprise one or more of silicon, silicon oxide, silicon nitride, titanium oxide, a composite material mixed in a preset ratio and direct-gap semiconductor materials; and the nanostructure comprises one or more of nanodot two-dimensional materials, nanopillar two-dimensional materials, and nanowire two-dimensional materials.

16. The optical artificial neural network intelligent chip of claim 1, wherein the optical filter layer has a thickness of $0.1\lambda \sim 10\lambda$, wherein $\lambda$ represents the center wavelength of the incident light.

17. The optical artificial neural network intelligent chip of claim 1, wherein the image sensor is one or more of the following:
CMOS image sensor (CIS), charge coupled device (CCD), single photon avalanche diode (SPAD) array and focal plane photodetector array.

18. The optical artificial neural network intelligent chip of claim 1, wherein the artificial neural network comprises a feedforward neural network.

19. The optical artificial neural network intelligent chip of claim 1, wherein a light-permeable medium layer is provided between the optical filter layer and the image sensor.

20. The optical artificial neural network intelligent chip of claim 1, wherein the image sensor is a front-side illuminated type, and comprises a metal wire layer and a light detection layer arranged from top to bottom, and the optical filter layer is integrated on a side of the metal wire layer away from the light detection layer;
wherein the image sensor is a back-side illuminated type, and comprises a light detection layer and a metal wire layer arranged from top to bottom, and the optical filter layer is integrated on a side of the light detection layer away from the metal wire layer.

21. An intelligent processing apparatus, comprising the optical artificial neural network intelligent chip according to claim 1.

22. The intelligent processing apparatus of claim 21, comprising one or more of smart phones, smart computers, intelligent identification devices, intelligent perception devices, and intelligent decision devices.

23. A method for preparing the optical artificial neural network intelligent chip of claim 1, comprising:
preparing an optical filter layer containing an optical modulation structure on a surface of a photosensitive area of an image sensor;
generating a processor with the functions of fully connected processing and nonlinear activation processing of signals; and
connecting the image sensor and the processor;
wherein the optical filter layer is configured to modulate, with different spectra, incident light which is incident to different location points of the optical modulation structure respectively by the optical modulation structure, to obtain information carried in the incident light corresponding to different location points on the surface of the photosensitive area; information carried in the incident light comprises light intensity distribution information, spectral information, angle information of the incident light and phase information of the incident light; and
the image sensor is configured to convert information carried in the incident light corresponding to different location points after being modulated by the optical filter layer into electric signals corresponding to the different location points, and send the electric signals corresponding to the different location points to the processor; the processor is configured to perform fully connected processing and nonlinear activation processing on the electrical signals corresponding to the different location points to obtain output signals of the artificial neural network; and the electrical signals are image signals modulated by the optical filter layer.

24. The method for preparing the optical artificial neural network intelligent chip of claim 23, wherein the preparing an optical filter layer containing an optical modulation structure on a surface of a photosensitive area of an image sensor comprises:

growing one or more layers of preset materials on the surface of the photosensitive area of the image sensor;

etching a pattern of the optical modulation structure on the one or more layers of preset materials to obtain the optical filter layer containing the optical modulation structure; or performing imprint transfer on the one or more layers of preset materials to obtain the optical filter layer containing the optical modulation structure; or performing additional dynamic modulation on the one or more layers of preset materials to obtain the optical filter layer containing the optical modulation structure; or performing zonal printing on the one or more layers of preset materials to obtain the optical filter layer containing the optical modulation structure; or performing zonal growth on the one or more layers of preset materials to obtain the optical filter layer containing the optical modulation structure; or performing quantum dot transfer on the one or more layers of preset materials to obtain the optical filter layer containing the optical modulation structure.

25. The method for preparing the optical artificial neural network intelligent chip of claim 23, wherein when the optical artificial neural network intelligent chip is used for the intelligent processing task of the target object, an optical modulation structure, an image sensor and an processor satisfying the training convergence condition are obtained by training the optical artificial neural network intelligent chip containing different optical modulation structures, image sensors, and processors with different fully connected parameters and nonlinear activation parameters using input training samples and output training samples corresponding to the intelligent processing task.

* * * * *